(12) United States Patent
Choi et al.

(10) Patent No.: US 12,186,576 B2
(45) Date of Patent: Jan. 7, 2025

(54) ENERGY CONCENTRATION APPARATUS HAVING CENTRAL HOLE AND MICRO-SLIT

(71) Applicant: UIF (University Industry Foundation), Yonsei University, Seoul (KR)

(72) Inventors: Heon Jin Choi, Seoul (KR); Jae Suk Sung, Suwon-si (KR)

(73) Assignee: UIF (UNIVERSITY INDUSTRY FOUNDATION), YONSEI UNIVERSITY, Seoul (KR)

( * ) Notice: Subject to any disclaimer, the term of this patent is extended or adjusted under 35 U.S.C. 154(b) by 859 days.

(21) Appl. No.: 17/337,718

(22) Filed: Jun. 3, 2021

(65) Prior Publication Data
US 2022/0008740 A1 Jan. 13, 2022

(30) Foreign Application Priority Data

Jul. 7, 2020 (KR) .................. 10-2020-0083376

(51) Int. Cl.
*A61N 2/00* (2006.01)
*A61N 2/02* (2006.01)
*H01Q 7/00* (2006.01)
*H01Q 13/10* (2006.01)

(52) U.S. Cl.
CPC .............. *A61N 2/006* (2013.01); *A61N 2/02* (2013.01); *H01Q 7/00* (2013.01); *H01Q 13/106* (2013.01)

(58) Field of Classification Search
CPC .......... A61N 2/006; A61N 2/008; A61N 2/02; A61N 2/06; A61N 1/40; A61N 1/403; A61N 1/406; A61N 1/36; A61N 1/36014; A61N 1/36017; A61N 1/36021; H01Q 13/10; H01Q 13/106; H01Q 13/12
See application file for complete search history.

(56) References Cited

U.S. PATENT DOCUMENTS

2002/0111614 A1* 8/2002 Werny .................. A61N 2/12 606/33

FOREIGN PATENT DOCUMENTS

| JP | 63-084103 | | 4/1988 |
|---|---|---|---|
| JP | S6384103 A | * | 4/1988 |
| KR | 10-2018-0051314 | | 5/2018 |
| KR | 20180051314 A | * | 5/2018 |
| KR | 10-2020-0038844 | | 4/2020 |

* cited by examiner

*Primary Examiner* — Kendra D Carter
*Assistant Examiner* — Jaeick Jang
(74) *Attorney, Agent, or Firm* — LEX IP MEISTER, PLLC

(57) ABSTRACT

An energy concentration apparatus is disclosed. The energy concentration apparatus includes a body part; a loop antenna coil part disposed on the body part; and a cover part coupled to the body part in order to cover the loop antenna coil part. The cover part has a central hole and a micro-slit.

20 Claims, 29 Drawing Sheets

Upper plate

Lower plate

Combined plate

Combined plate

Upper plate

Lower plate

Combined plate

Combined plate

Upper plate

Lower plate

Combined plate

Upper plate

Lower plate

Combined plate

Combined plate

Upper plate

Lower plate

Combined plate

Upper plate

Lower plate

ENERGY CONCENTRATION APPARATUS HAVING CENTRAL HOLE AND MICRO-SLIT

CROSS-REFERENCE TO RELATED APPLICATION

This application claims the benefit of Korean Patent Application No. 10-2020-0083376 filed on Jul. 7, 2020, which is hereby incorporated by reference herein in its entirety.

BACKGROUND

1. Technical Field

The present invention relates generally to an energy concentration apparatus, and more particularly to an energy concentration apparatus having a central hole and a micro-slit.

2. Description of the Related Art

Recently, research is being conducted to acquire a new characteristic by changing a cell itself or changing a physical property of an area near a cell in such a way as to generate a magnetic or electric field in a microscopic area such as a cell and then apply stimulation to the cell using the field energy.

Furthermore, research into schemes of treating nerve-related problems, such as a scheme of applying stimulation and reducing pain by radiating such energy onto the nerves of the human body, is also being actively conducted.

In general, as a method of applying energy, there is used a method that changes a physical property of a cell or applies stimulation to a nerve using energy such as a magnetic field or electric field formed by forming an electrode of a predetermined shape and then applying a current or voltage to the electrode.

In this case, it is a common method to apply a high current or voltage to the electrode in order to obtain a large amount of energy. Therefore, a problem arises in that a large amount of power is required to obtain a large amount of energy, and in turn a problem arises in that a dangerous influence may be imposed on the human body.

Moreover, since field energy such as a magnetic field or electric field is characterized in that it spreads over a wide range, it is considerably difficult to radiate energy only onto a specific area, especially a considerably small area.

Related Art Document

Patent document 1: Korean Patent Application Publication No. 10-2020-0038844 (published on Apr. 14, 2020)

SUMMARY

An energy concentration apparatus having a central hole and a micro-slit according to the present invention have the following objects:

A first object of the present invention is to obtain high energy by concentrating the energy formed on an electrode.

A second object of the present invention is to adjust the area to which energy is applied as desired by allowing energy to be radiated only onto a specific area of interest.

A third object of the present invention is to adjust the magnitude and region of concentrated energy by additionally forming a micro-slit structure over an electrode.

The objects of the present invention are not limited to those mentioned above, and other objects that are not mentioned above will be clearly understood by those skilled in the art from the following description.

According to an aspect of the present invention, there is provided an energy concentration apparatus having a central hole and a micro-slit, the energy concentration apparatus including: a body part; a loop antenna coil part disposed on the body part; and a cover part coupled to the body part in order to cover the loop antenna coil part; wherein the cover part has a central hole and a micro-slit.

According to another aspect of the present invention, there is provided an energy concentration apparatus having a central hole and a micro-slit, the energy concentration apparatus including: a body part; a loop antenna coil part disposed on the body part; a lower cover part coupled to the body part in order to cover the loop antenna coil part; an upper cover part coupled to the top surface of the lower cover part in a corresponding shape; a drive unit configured to drive the upper cover part; and a control unit configured to control the drive unit; wherein the lower cover part includes a lower central hole and at least one lower micro-slit, and the upper cover part includes an upper central hole and at least one upper micro-slit; and wherein at least one of the lower cover part and the upper cover part is rotatably provided, and an exposed space is variable as the central holes and the micro-slits overlap each other through rotation.

In an embodiment, the cover part or lower and upper cover parts may be made of an electrically conductive material, and the bottom surface of the body part may be provided with a magnetic material.

In an embodiment, the micro-slit of each cover part may be formed to continuously connect the central hole of the cover part and the outer circumference of the cover part.

In an embodiment, each micro-slit may be formed such that the width of the outer end thereof in contact with the outer circumference is wider than the width of the inner end thereof in contact with the central hole.

In an embodiment, each micro-slit may be formed such that the width of the outer end thereof in contact with the outer circumference is narrower than the width of the inner end thereof in contact with the central hole.

In an embodiment, each micro-slit may be formed such that the width of the central portion thereof is wider than the width of the inner and outer ends thereof.

In an embodiment, each micro-slit may be formed such that the width of the central portion thereof is narrower than the width of the inner and outer ends thereof.

In an embodiment, energy may be selectively concentrated by adjusting the diameter of each central hole, the width of each micro-slit, and/or the number of turns of a coil wound in the loop antenna coil part.

In an embodiment, the upper micro-slit may have a width that is equal to or narrower than the width of the lower micro-slit.

In an embodiment, the lower cover part may include one lower micro-slit, the upper cover part may include a plurality of upper micro-slits having different widths, and the widths of the upper micro-slits may be equal to or narrower than a width of the lower micro-slit.

In an embodiment, when at least one of the lower and upper cover parts is rotated, the upper micro-slit may overlap the lower micro-slit.

In an embodiment, each of the central holes may have an oval shape or eccentric circle shape; and, when at least one of the lower and upper cover parts is rotated, the exposed space of the central holes may be variable as the central holes partially overlap each other.

In an embodiment, each of the central holes may have an elongated polygonal shape; and, when at least one of the lower and upper cover parts is rotated, the exposed space of the central holes may be variable as the central holes partially overlap each other.

BRIEF DESCRIPTION OF THE DRAWINGS

The above and other objects, features, and advantages of the present invention will be more clearly understood from the following detailed description taken in conjunction with the accompanying drawings, in which.

DETAILED DESCRIPTION

Figure 1A:
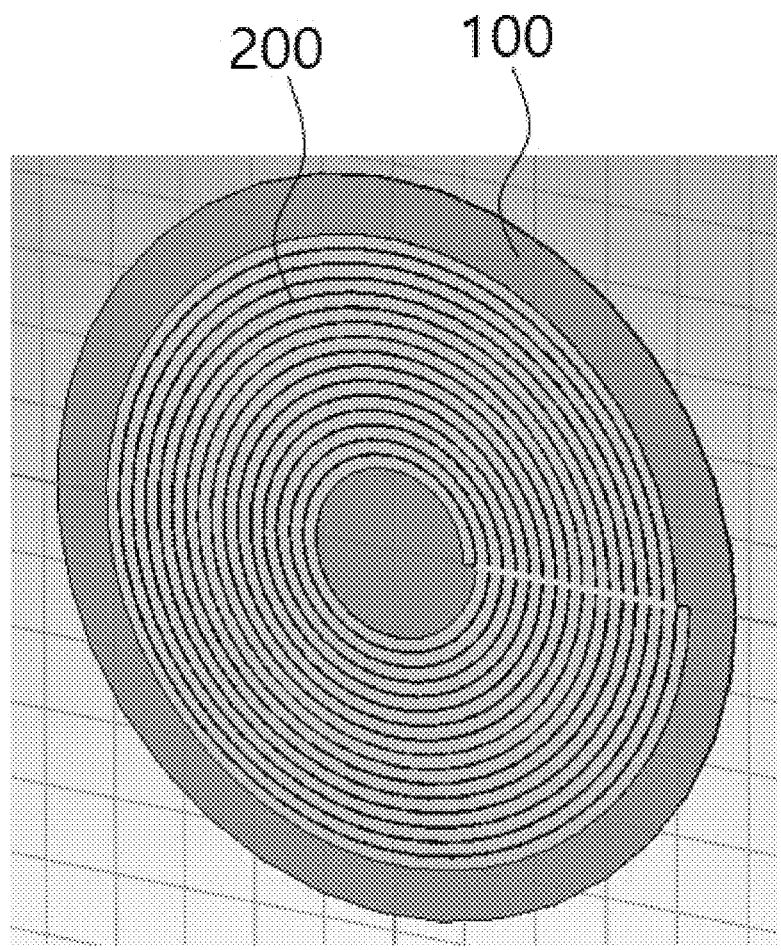
FIGS. 1(a) and 1(b) show energy concentration apparatus according to an embodiment of the present invention, which includes a body part, a loop antenna coil part, and a single cover part.

Embodiments of the present invention will be described in detail below with reference to the accompanying drawings so that those of ordinary skill in the art can easily implement the present invention. As can be easily understood by those of ordinary skill in the art to which the present invention pertains, the following embodiments may be modified in various forms without departing from the spirit and scope of the present invention. The same or similar parts are denoted by the same reference symbols throughout the drawings as much as possible.

The terminology used therein is intended merely to refer only to specific embodiments, and is not intended to limit the present invention. The singular forms used herein also include plural forms unless clearly indicated to the contrary.

The term "including" used herein is intended to specify particular features, regions, integers, steps, acts, elements, and/or components, and is not intended to exclude the presence or addition of another specific feature, region, integer, step, action, element, component, and/or a group thereof.

All the terms including technical and scientific terms used herein have the same meanings as commonly understood by those of ordinary skill in the art to which the present invention pertains. The terms defined in the dictionaries are further interpreted as having meanings consistent with the related technical literature and the present disclosure, and are not interpreted in ideal or overly formal senses unless expressly so defined herein.

The present invention is directed to an energy concentration apparatus, which may be used as a bio-stimulation apparatus that is inserted into the human body and intensively radiates energy such as an electric field or a magnetic field onto a specific part of the human body.

However, the present invention is not limited thereto, and may be used in various fields where energy concentration by the present invention can be utilized.

Hereinafter, the present invention will be described with reference to the drawings. For reference, the drawings may be partially exaggerated in order to describe the features of the present invention. In this case, it is preferable to perform interpretation in light of the overall purport of the present specification.

The present invention is directed to a technology that concentrates generated energy and adjusts the amount and region of energy by forming a micro-slit and a central hole in a cover part provided to cover an electrode with and adjusting one or more factors such as the shape, positions, and number of one or more micro-slits, the size of a central hole, and/or the number of turns of a coil.

The present invention is directed to an energy concentration apparatus having a central hole and a micro-slit, and may include both a first embodiment provided with a single cover part and a second embodiment provided with a rotatable cover part in a dual structure.

First, the first embodiment provided with a single cover part will be described below (see FIG. 1).

The present invention is directed to an energy concentration apparatus having a central hole and a micro-slit, the energy concentration apparatus including: a body part 100; a loop antenna coil part 200 disposed on the body part 100; and a cover part 300 coupled to the body part 100 in order to cover the loop antenna coil part 200, wherein the cover part 300 may have a central hole 310 and a micro-slit 320.

Figure 2:
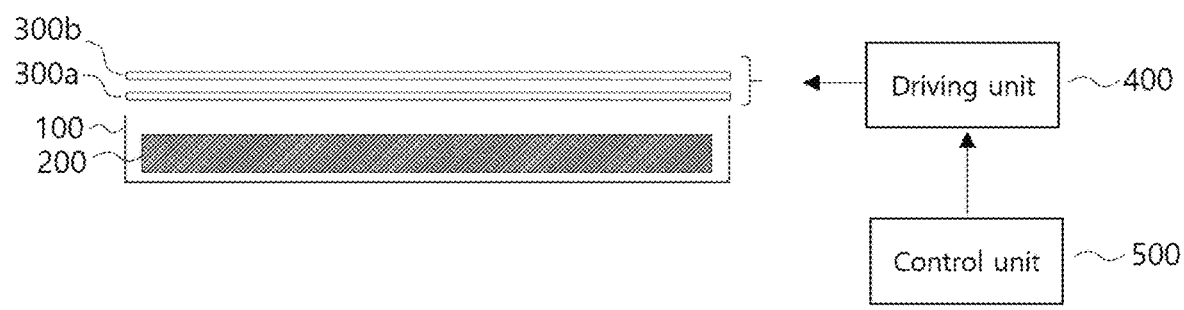
FIG. 2 shows an energy concentration apparatus according to an embodiment of the present invention, which includes a body part, a loop antenna coil part, an upper cover part, and a lower cover part.

Next, the second embodiment provided with a rotatable cover part in a dual structure including an upper cover part and a lower cover part will be described (see FIG. 2).

The present invention is directed to an energy concentration apparatus having a central hole and a micro-slit, the energy concentration apparatus including: a body part 100; a loop antenna coil part 200 disposed on the body part 100; a lower cover part 300a coupled to the body part 100 in order to cover the loop antenna coil part 200; an upper cover part 300b coupled to the top surface of the lower cover part 300a in a corresponding shape; a drive unit 400 configured to drive the upper cover part 300b; and a control unit 500 configured to control the drive unit.

In the second embodiment, the lower cover part 300a may include a lower central hole 310a and at least one lower micro-slit 320a, and the upper cover part 300b may include an upper central hole 310b and at least one upper micro-slit 320b.

In the second embodiment, at least one of the lower cover part 300a and the upper cover part 300b may be rotatably provided, and an exposed space may be variable as the central holes and the micro-slits overlap each other through rotation.

The body part 100 according to the present invention is a component configured such that the loop antenna coil part 200 is disposed thereon, and may be provided in a flat plate shape or in a hollow shape in which the inside thereof is concave and empty.

The cover part 300 according to the present invention is a component coupled to the body part 100 in order to cover the loop antenna coil part 200 disposed on the body part 100, and has a shape appropriately selected to correspond to the shape of the body part 100.

The cover part 300 according to the present invention may be made of an electrically conductive material, and the bottom surface of the body part 100 may be provided with a magnetic material. This configuration is intended to allow energy such as a magnetic field to be emitted from the top side of the body part 100, i.e., from the cover part 300. In other words, the reason why a magnetic field is emitted not from the bottom side of the body part 100 but only from the top side of the body part 100 is that there is employed a structure in which a magnetic material is disposed on the bottom surface of the body part 100 to shield a magnetic field when a coil electrode is formed.

Figure 1B:
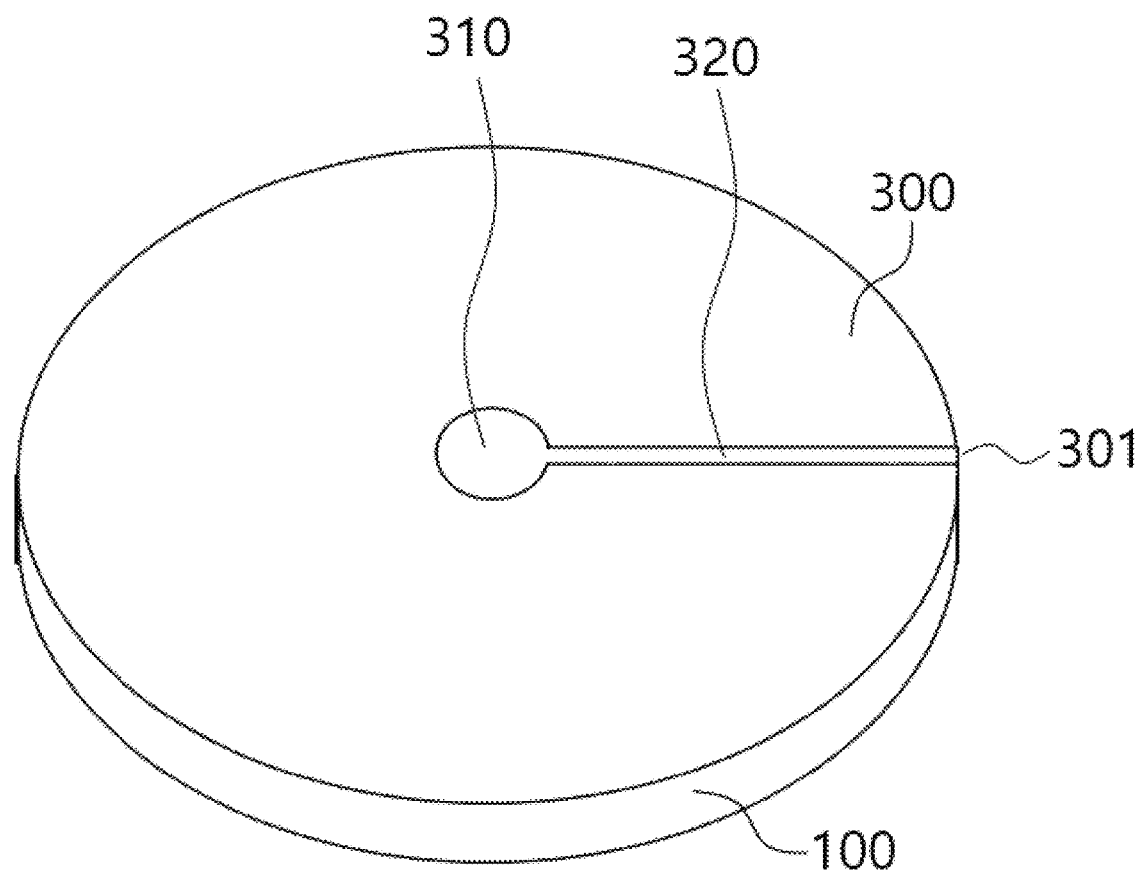

In the present invention, each of the micro-slits 320, 320a, and 320b of the cover parts 300, 300a, and 300b may be formed to continuously connect a corresponding one of the central holes 310, 310a, and 310b and the outer circumference 301 of a corresponding one of the cover parts 300, 300a, and 300b (see FIG. 1).

Figure 6A:
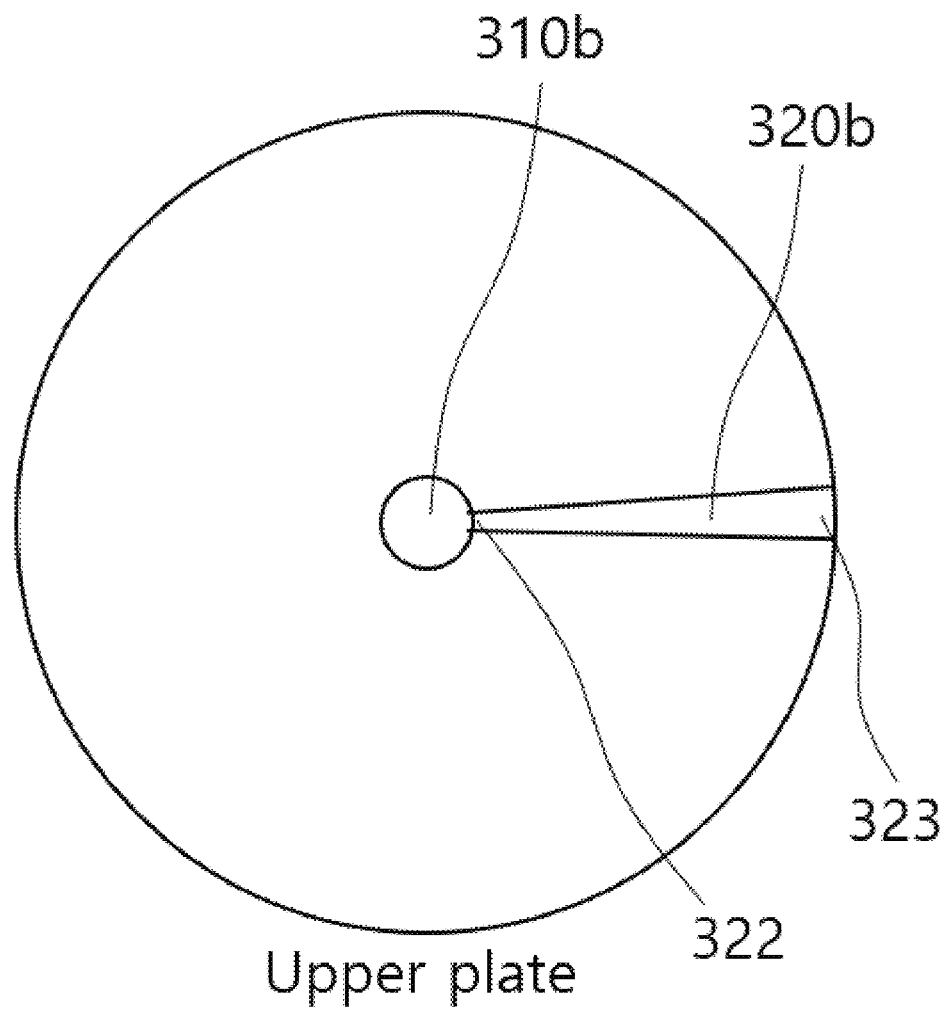
FIGS. 6(a) and 6(b) show energy concentration apparatus according to an embodiment of the present invention, in which a micro-slit has a tapered shape.

In the present invention, each of the micro-slits 320, 320a, and 320b may be provided such that the width of the outer end 323 thereof in contact with a corresponding outer circumference 301 is wider than the width of the inner end 322 thereof in contact with a corresponding one of the central holes 310, 310a, and 310b (see FIG. 6(a)).

Figure 6B:
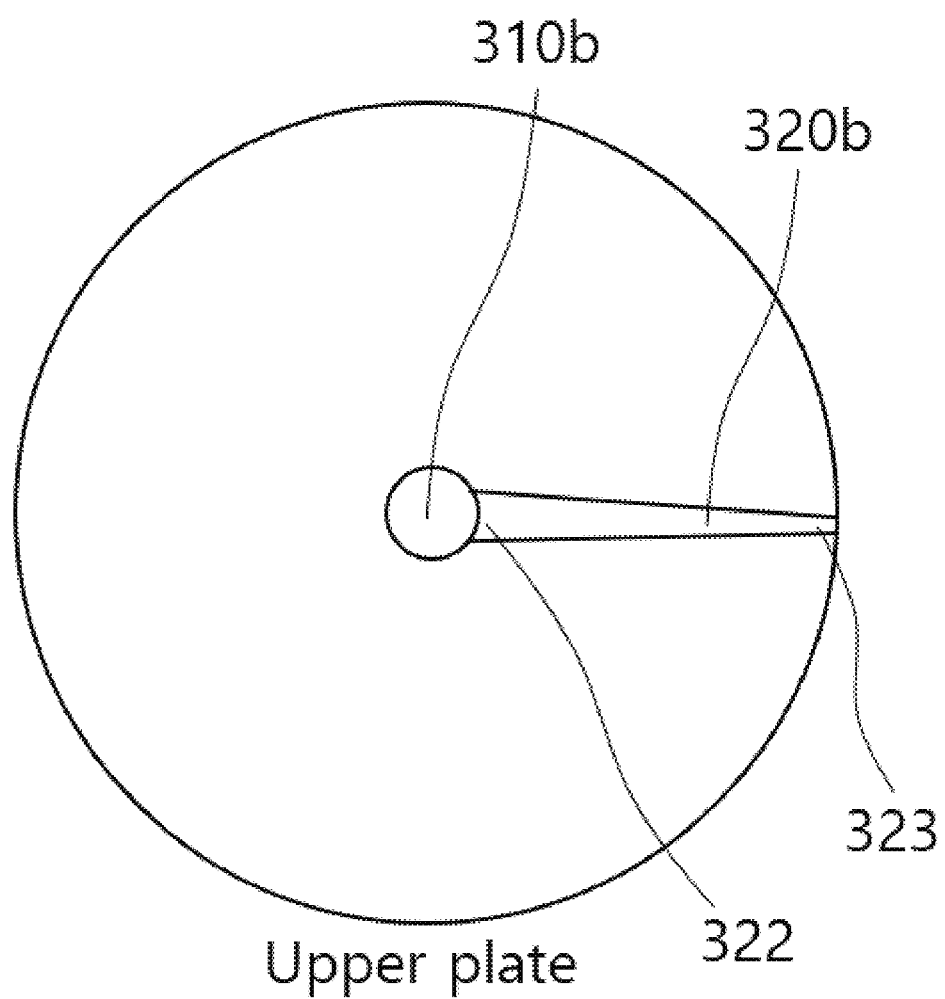

In the present invention, each of the micro-slits 320, 320a, and 320b may be provided such that the width of the outer end 323 thereof in contact with a corresponding outer circumference 301 is narrower than the width of the inner end 322 thereof in contact with a corresponding one of the central holes 310, 310a, and 310b (see FIG. 6(b)).

Figure 8A:
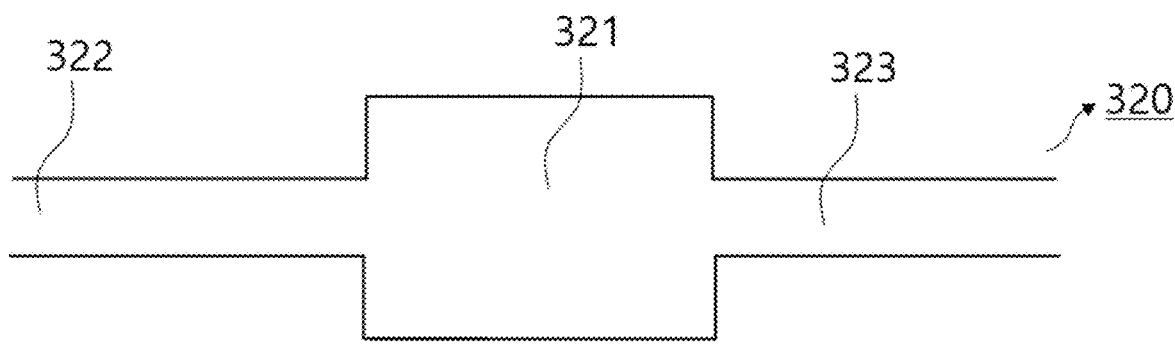
FIGS. 8(a) and 8(b) shows embodiments regarding the shapes of micro-slits according to the present invention, in which the width of the central portion thereof is different from the width of the ends thereof.

In the present invention, the micro-slit may be provided such that the width of the central portion 321 thereof is wider than the width of the inner and outer ends 322 and 323 thereof (see FIG. 8(a)).

Figure 8B:
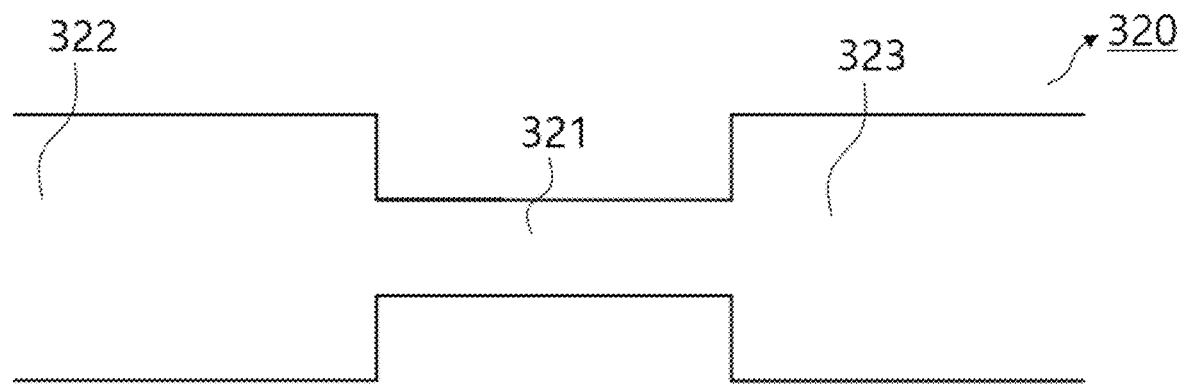

In the present invention, the micro-slit may be provided such that the width of the central portion 321 thereof is narrower than the width of the inner and outer ends 322 and 323 thereof (see FIG. 8(b)).

In the present invention, energy may be selectively concentrated by adjusting the diameter of the central hole 310, the width of the micro-slit 320, and the number of turns of a coil wound in the loop antenna coil part 200.

In the second embodiment of the present invention, the upper micro-slit 320b may be provided such that the width thereof is equal to or narrower than the width of the lower micro-slit 320a. Due to this structure, adjustment may be performed such that when the upper cover part and the lower cover part are rotated and completely overlap each other, the width of the upper micro-slit is equal to or narrower than the width of the lower micro-slit.

Meanwhile, depending on the degree of overlapping, an adjustment may be made to form a space smaller than the width of the lower micro-slit.

The second embodiment according to the present invention will be described in greater detail below.

In the second embodiment, the lower cover part 300a may include one lower micro-slit 320a, the upper cover part 300b may include a plurality of upper micro-slits 320b having different widths, and the widths of the upper micro-slits 320b may be equal to or narrower than the width of the lower micro-slit 320a (see FIG. 3).

The present embodiment may be provided in a structure in which when at least one of the lower and upper cover parts 300a and 300b is rotated, the upper micro-slit 320b overlaps the lower micro-slit 320a.

In the second embodiment, both the lower and upper cover parts 300a and 300b may be rotated, or only one of the lower and upper cover parts 300a and 300b may be rotated. The reason for this is that since the present embodiment is characterized by overlapping the micro-slits and central holes of the lower and upper cover parts through rotation, overlapping can be achieved even by rotating only one of them.

If a plurality of micro-slits is provided in each of the lower and upper cover parts and both the cover parts are rotated, the number of embodiments implemented by overlapping the micro-slits may be increased.

Meanwhile, the lower and upper cover parts may be driven by the drive unit 400, and the drive unit 400 may be controlled by the control unit 500. The configurations of the drive unit 400 and the control unit 500 may be implemented in a variety of known methods. The control unit 500 may not be disposed inside the energy concentration apparatus, but may be disposed outside the body part and control the drive unit 400 via a wireless connection.

Figure 3A:
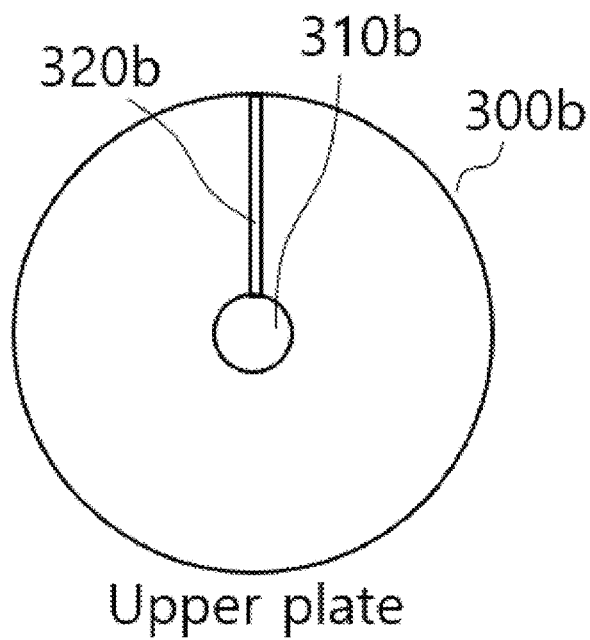
FIGS. 3(a), 3(b), 3(c) and 3(d) show energy concentration apparatus according to an embodiment of the present invention, in which one micro-slit is formed in each of upper and lower cover parts.
Figure 3B:
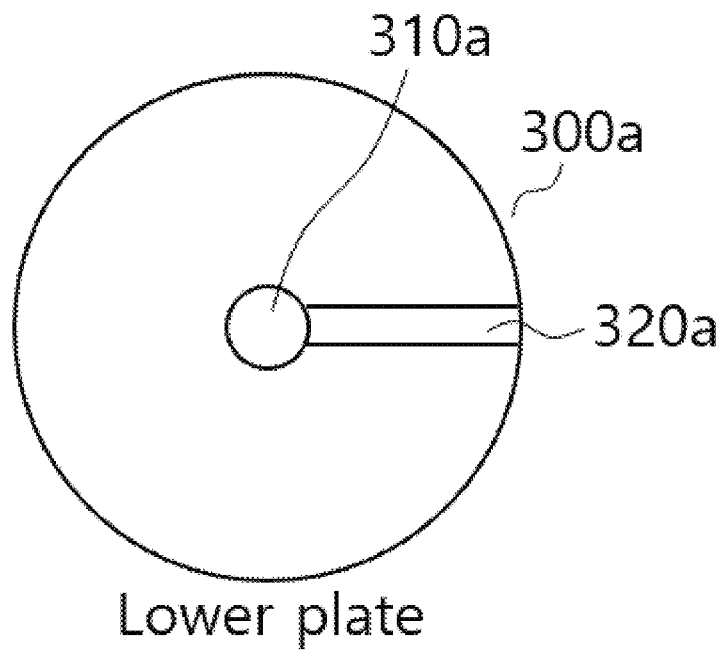
Figure 3C:
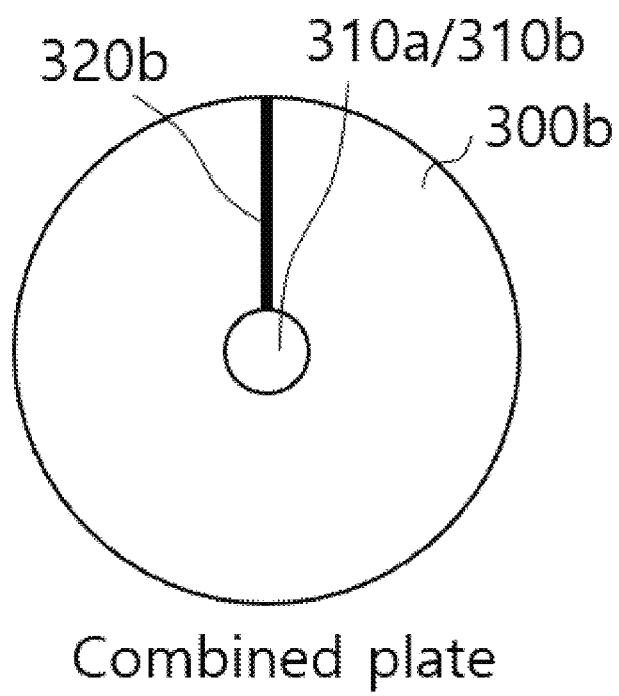
Figure 3D:
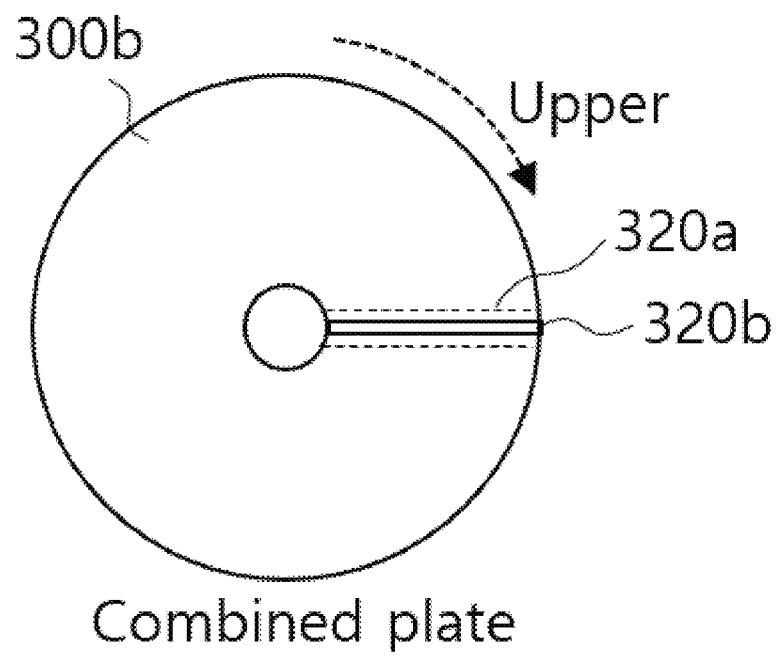

The operational structure of the second embodiment shown in FIG. 3 will be described as follows:

The upper cover part 300b includes one rectangular upper micro-slit 320b (see FIG. 3(a)), and the lower cover part 300a includes one rectangular lower micro-slit 320a larger than the upper micro-slit 320b (see FIG. 3(b)). When the lower and upper cover parts are coupled to each other, the lower micro-slit 320a is closed by the upper cover part 300b, the upper micro-slit 320b is closed by the lower cover part 300a, and only the lower central hole 310a and the upper central hole 310b overlap each other and are opened (see FIG. 3(c)). Meanwhile, when the upper cover part 300b is rotated clockwise so that the upper micro-slit 320b overlaps the lower micro-slit 320a, parts of the open space of the lower micro-slit are closed by the upper cover part, and only the space of the upper micro-slit 320b is opened (see FIG. 3(d)).

Figure 4A:
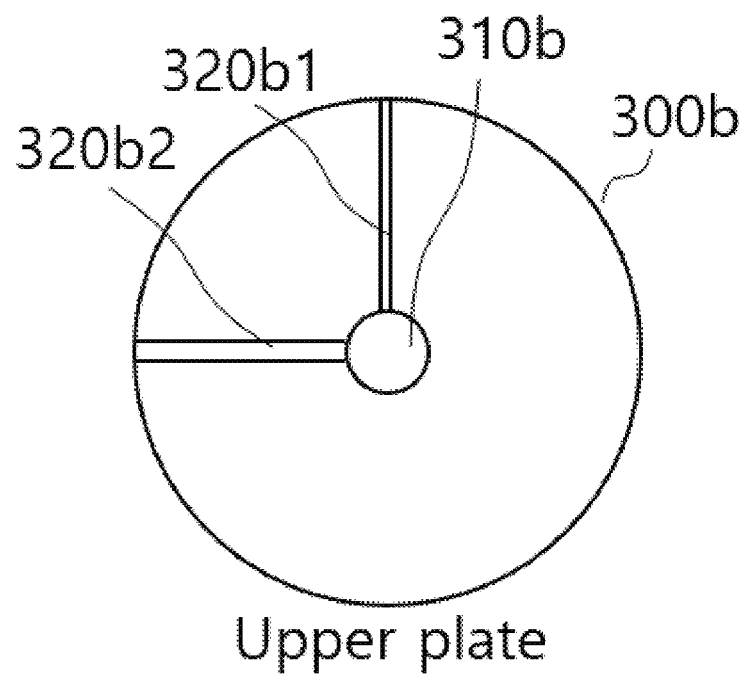
FIGS. 4(a), 4(b), 4(c) and 4(d) show energy concentration apparatus according to an embodiment of the present invention, in which two micro-slits are formed in an upper cover part and one micro-slit is formed in a lower cover part.
Figure 4B:
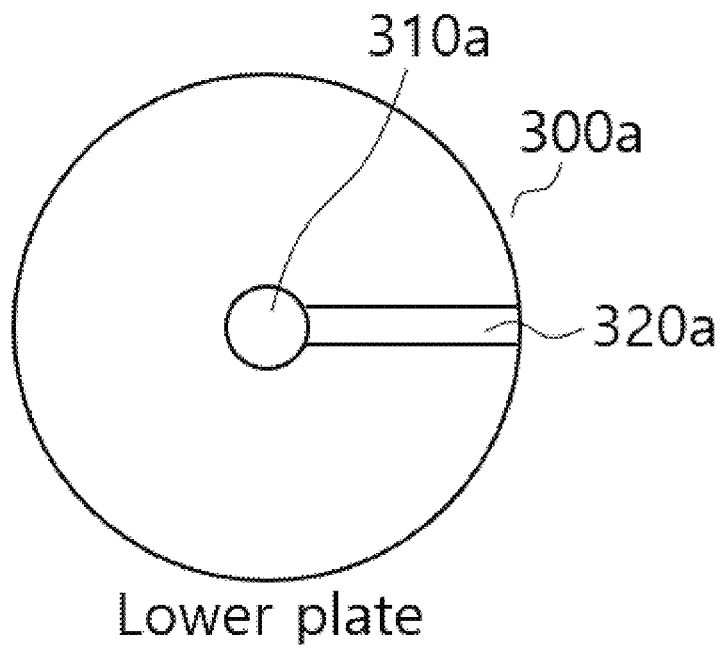
Figure 4C:
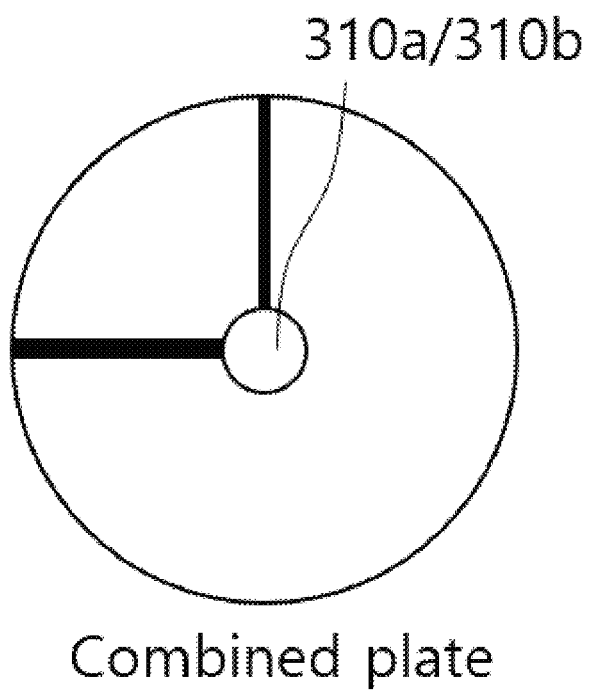
Figure 4D:
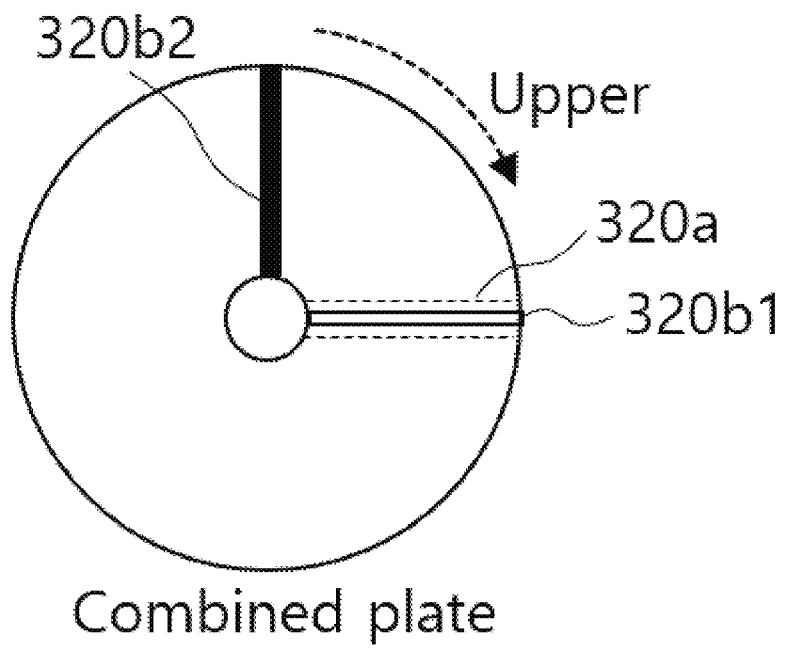

The operational structure of the second embodiment shown in FIG. 4 will be described as follows:

The upper cover part 300b includes two rectangular upper micro-slits 320b1 and 320b2 having different widths (see FIG. 4(a)), and the lower cover part 300a includes one rectangular lower micro-slit 320a having a width larger than the widths of the upper micro-slits 320b1 and 320b2 (see FIG. 4(b)). When the lower and upper cover parts are coupled to each other, the lower micro-slit 320a is closed by the upper cover part 300b, the upper micro-slits 320b1 and 320b2 are closed by the lower cover part 300a, and only the lower central hole 310a and the upper central hole 310b overlap each other and are opened (see FIG. 4(c)). Meanwhile, when the upper cover part 300b is rotated clockwise so that the upper micro-slit 320b1 overlaps the lower micro-slit 320a, parts of the open space of the lower micro-slit 320a are closed by the upper cover part 300b and only the space of the upper micro-slit 320b1 is opened (see FIG. 4(d)). Furthermore, when the upper cover part 300b is further rotated clockwise, the upper micro-slit 320b2 may overlap the lower micro-slit 320a and be opened.

Figure 5A:
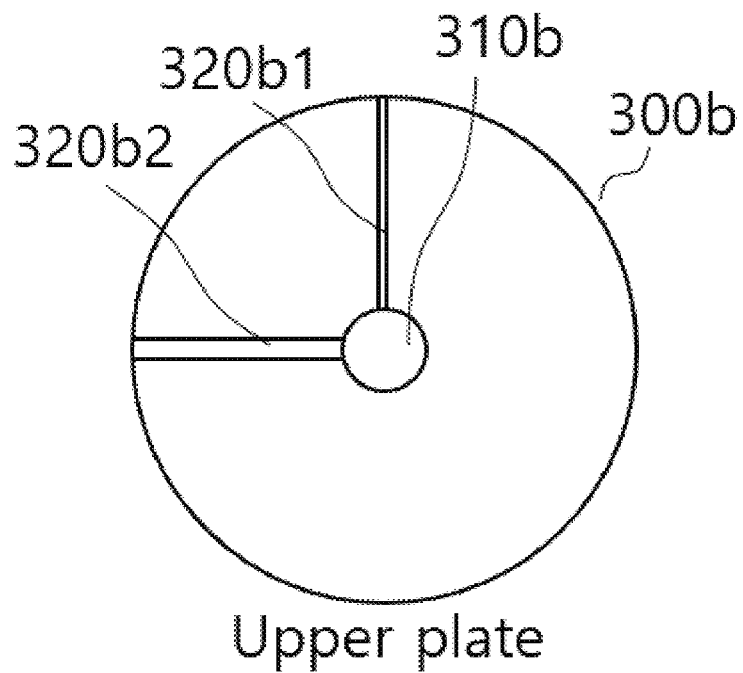
FIGS. 5(a), 5(b), 5(c), 5(d) and 5(e) show energy concentration apparatus according to an embodiment of the present invention, in which two micro-slits are formed in an upper cover part and two micro-slits are formed in a lower cover part.
Figure 5B:
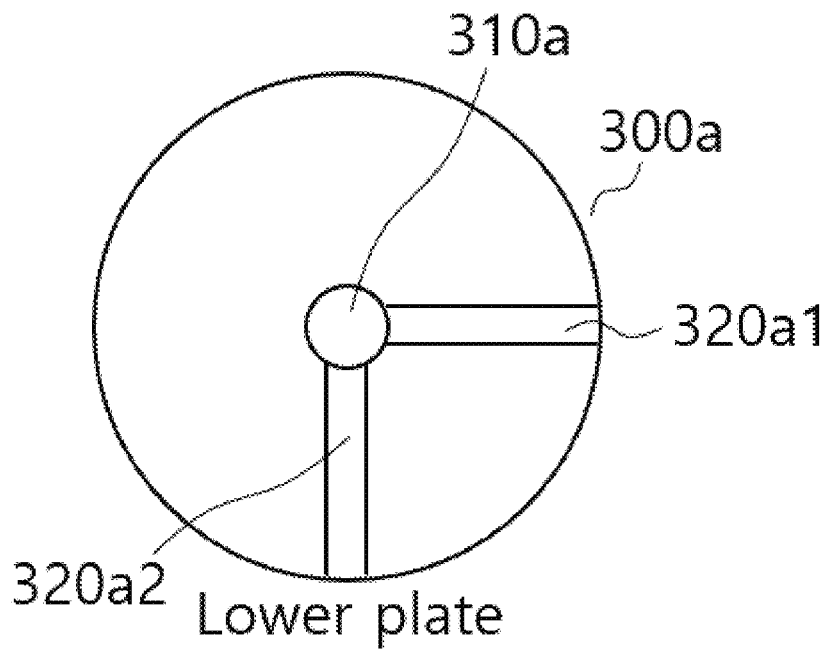
Figure 5C:
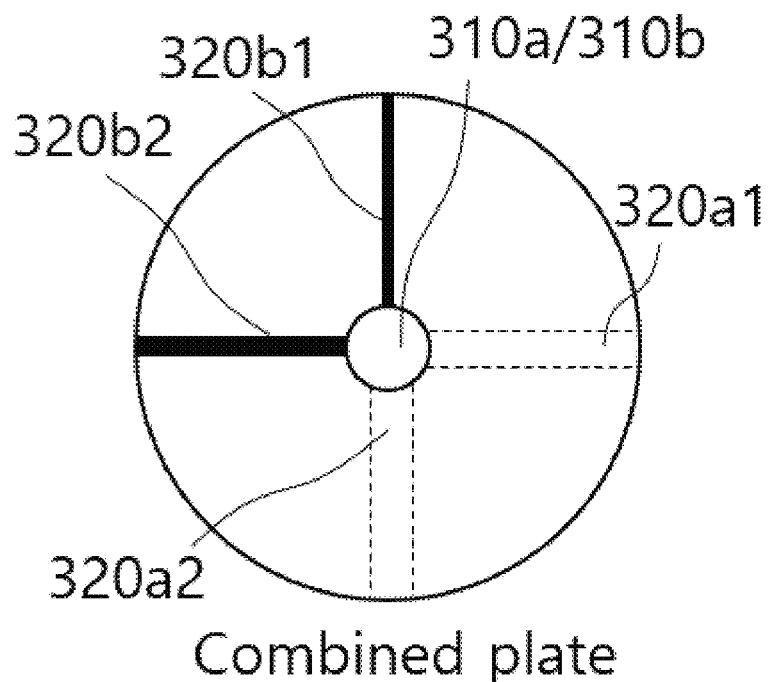
Figure 5D:
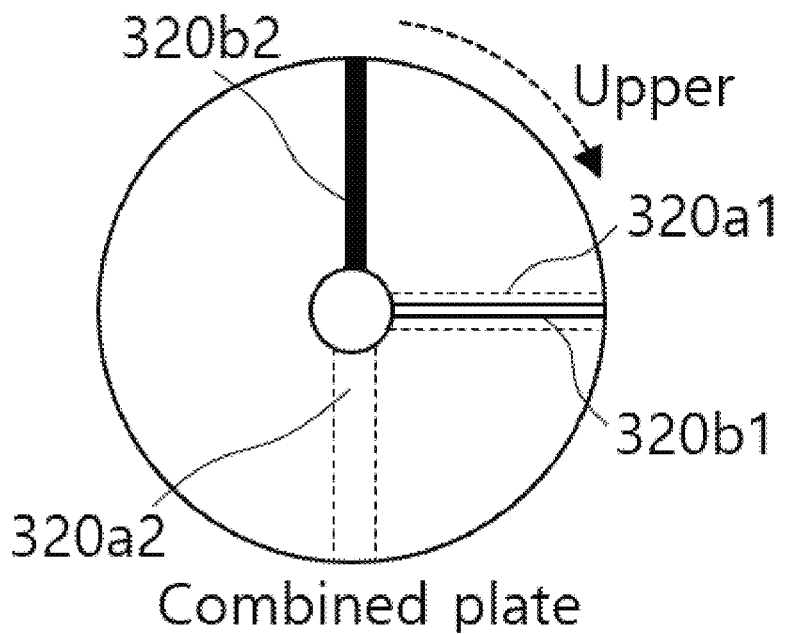
Figure 5E:
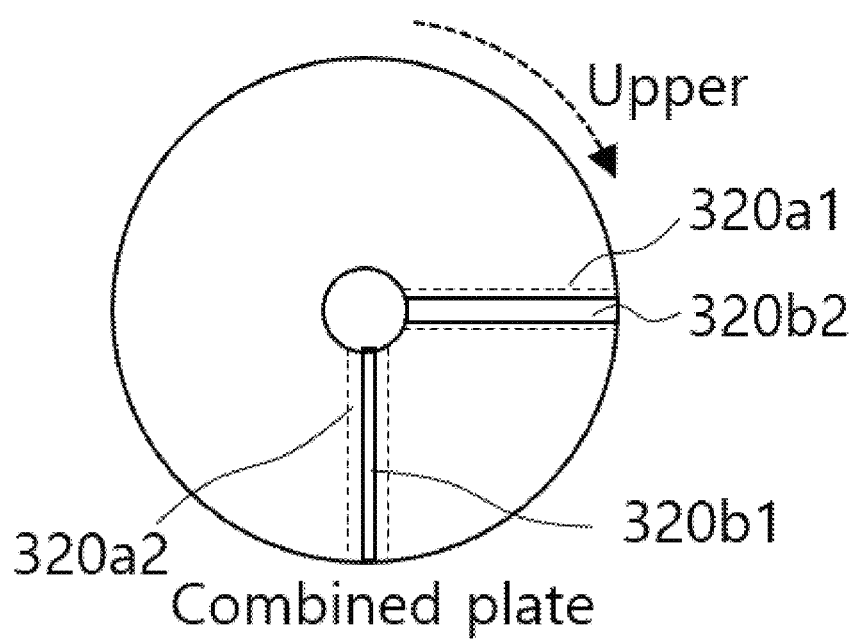

The operational structure of the second embodiment shown in FIG. 5 will be described as follows:

The upper cover part 300b includes two rectangular upper micro-slits 320b1 and 320b2 having different widths (see FIG. 5(a)), and the lower cover part 300a includes two rectangular lower micro-slits 320a1 and 320a2 having widths larger than the widths of the upper micro-slits 320a1 and 320a2 (see FIG. 5(b)). When the lower and upper cover part are coupled to each other, the lower micro-slits 320a1 and 320a2 are closed by the upper cover part 300b, the upper micro-slits 320a1 and 320a2 are closed by the lower cover part 300a, and only the lower central hole 310a and the upper central hole 310b overlap each other and are opened (see FIG. 5(c)). Meanwhile, when the upper cover part 300b is rotated clockwise so that the upper micro-slit 320b1 overlaps the lower micro-slit 320a1, parts of the open space of the lower micro-slit 320a1 are closed by the upper cover part 300b, and only the space of the upper micro-slit 320b1 is opened (see FIG. 5(d)). Furthermore, when the upper cover part 300b is further rotated clockwise, the upper micro-slit 320b1 overlaps the lower micro-slit 320a2 and is opened, and the upper micro-slit 320b2 overlaps the lower micro-slit 320a1 and is opened (see FIG. 5(e)).

Figure 7A:
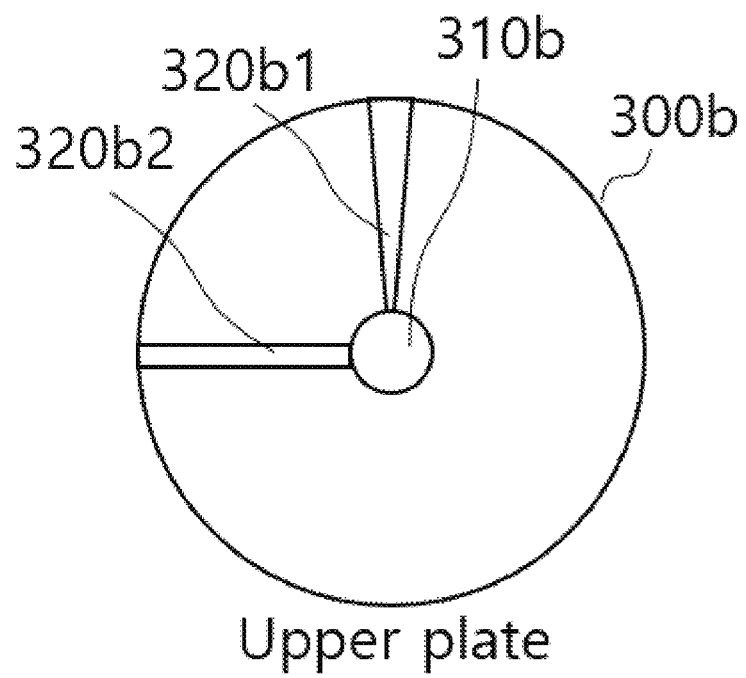
FIGS. 7(a), 7(b), 7(c), 7(d) and 7(e) show energy concentration apparatus according to an embodiment of the present invention, in which two micro-slits having a rectangular shape and a tapered shape, respectively, are formed in an upper cover part and one micro-slit having a rectangular shape is formed in a lower cover part.
Figure 7B:
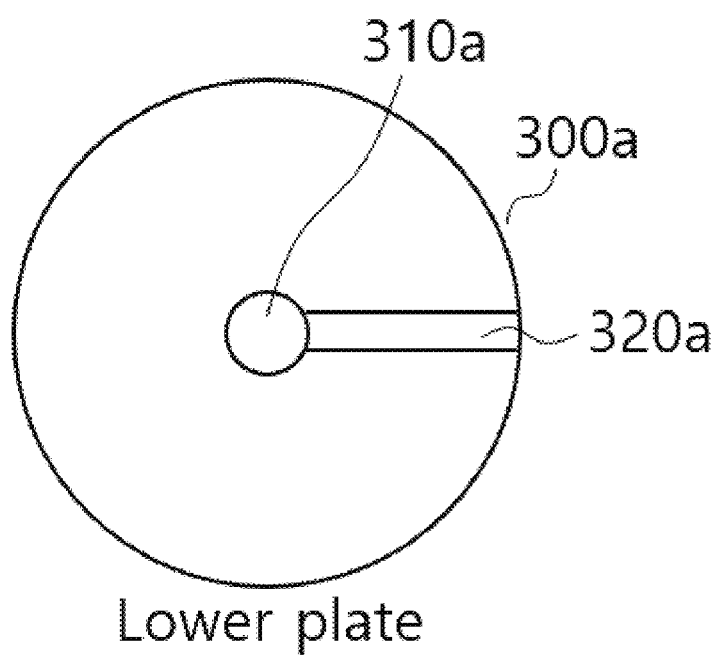
Figure 7C:
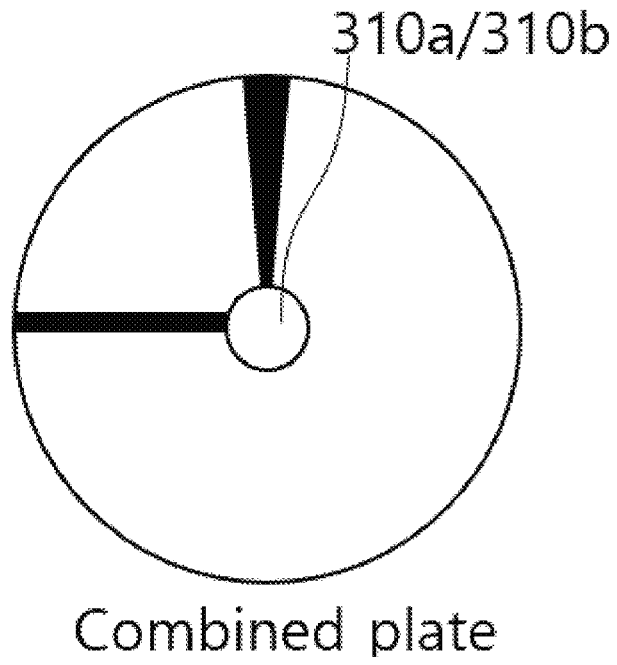
Figure 7D:
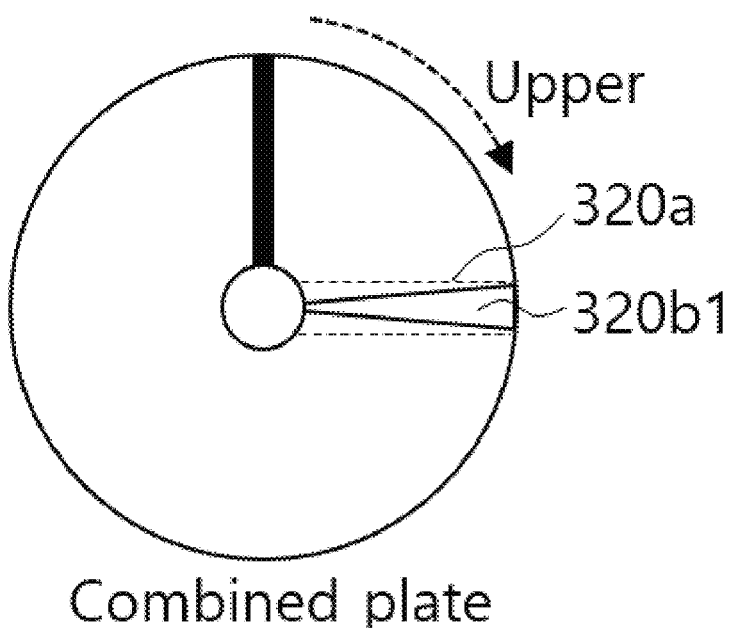
Figure 7E:
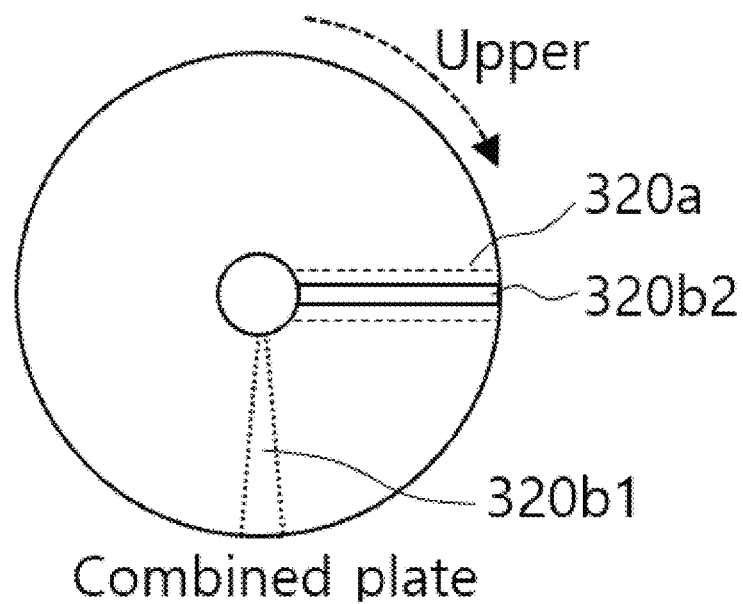

The operational structure of the second embodiment shown in FIG. 7 will be described as follows:

The upper cover part 300b includes one tapered cone-shaped upper micro-slit 320b1 and one rectangular upper micro-slit slit 320b2 (see FIG. 7(a)), and the lower cover part 300a includes one rectangular lower micro-slit 320a having a width wider than the widths of the upper micro-slits 320b1 and 320b2 (see FIG. 7(b)). When the lower and upper cover parts are coupled to each other, the lower micro-slit 320a is closed by the upper cover part 300b, the upper micro-slits 320b1 and 320b2 are closed by the lower cover part 300a, and only the central hole 310a and the upper central hole 310b overlap each other and are opened (see FIG. 7(c)). Meanwhile, when the upper cover part 300b is rotated clockwise so that the cone-shaped upper micro-slit 320b1 overlaps the lower micro-slit 320a, parts of the open space of the lower micro-slit 320a may be closed by the upper cover part 300b, and only the space of the upper micro-slit 320b1 is opened (see FIG. 7(d)). Furthermore, when the upper cover part 300b is further rotated clockwise, the upper micro-slit 320b2 overlaps the lower micro-slit 320a and is opened, and the upper micro-slit 320b1 is closed by the lower cover part 300a (see FIG. 7(e)).

Meanwhile, the second embodiment according to the present invention may be provided such that central holes have different shapes and thus a space is variable as the central holes overlap each other through rotation.

FIGS. 9 and 10 illustrate an embodiment in which central holes have different shapes. For the convenience of description, micro-slits are excluded from the drawings.

However, it will be apparent that the above-described micro-slits having various structures may be combined with such a central hole configuration.

In the present invention, central holes may have an oval shape or eccentric circle shape, so that when at least one of lower and upper cover parts 300a and 300b is rotated, the exposed space of the central hole 310a is variable as the central holes partially overlap each other (see FIG. 9).

In the present invention, central holes may have an elongated polygonal shape so that when at least one of a lower cover part 300a and an upper cover part 300b is rotated, the exposed space of the central hole 310a is variable as the central holes partially overlap each other (see FIG. 10).

Figure 9A:
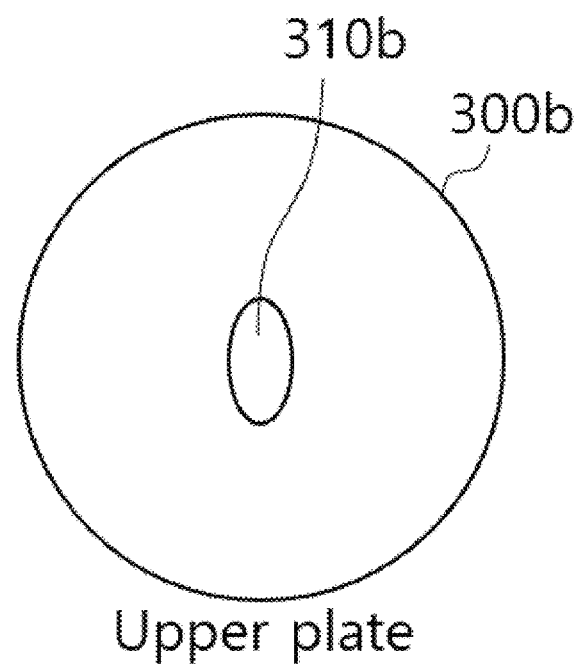
FIGS. 9(a), 9(b), 9(c), 9(d) and 9(e) show embodiments regarding the shape of central holes according to the present invention, in which the central holes have an oval shape.
Figure 9B:
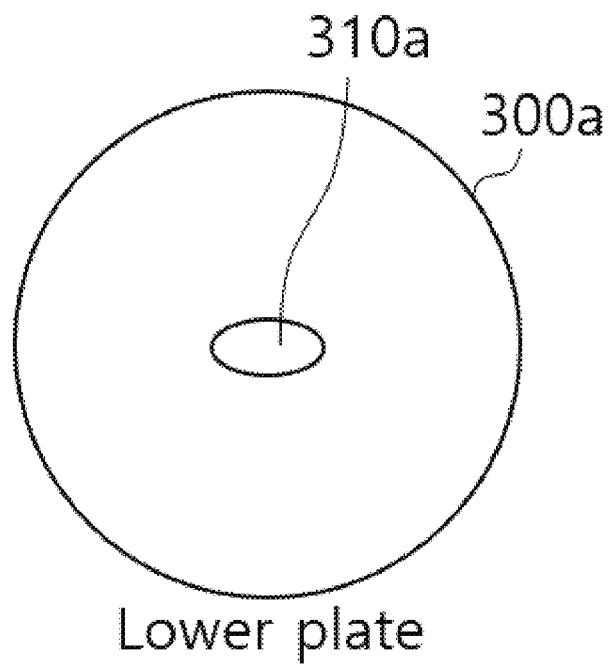
Figure 9C:
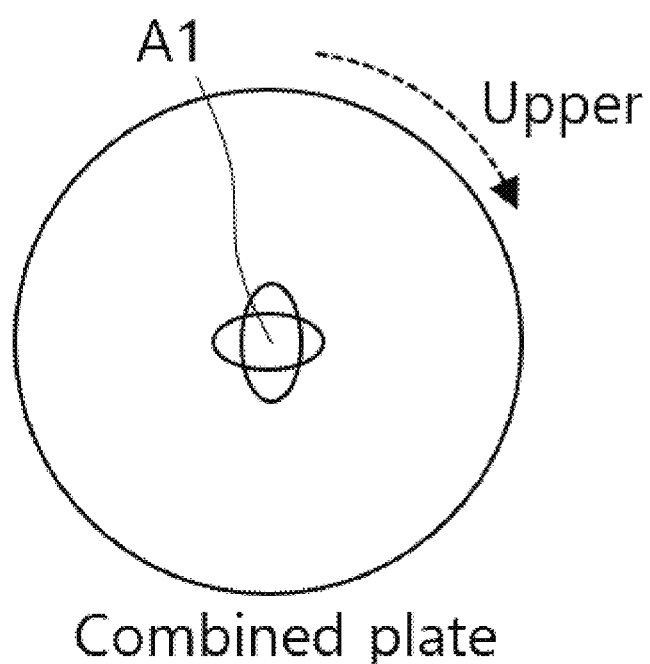
Figure 9D:
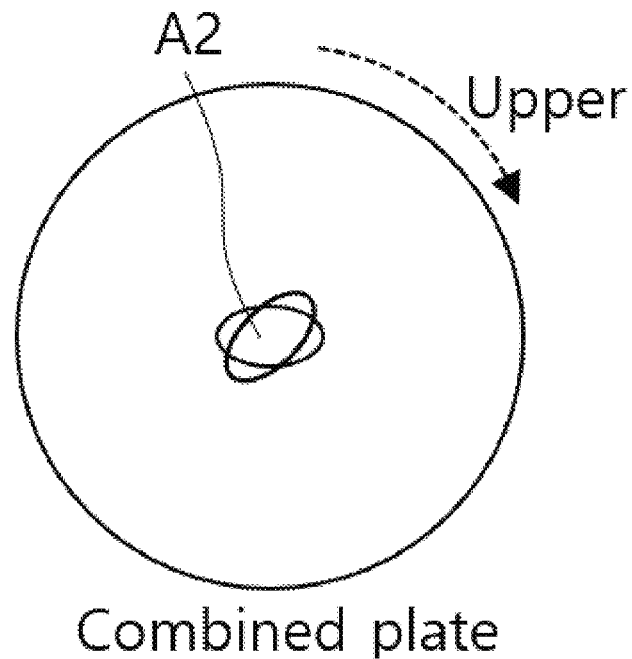
Figure 9E:
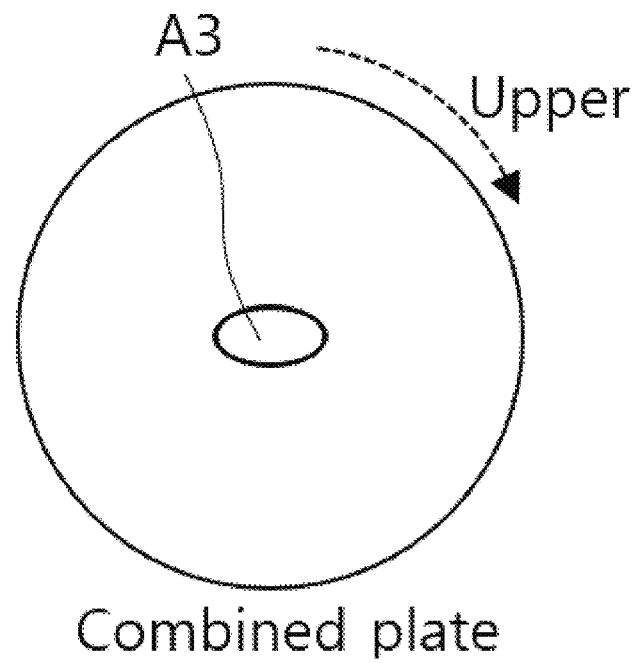

The operational structure of the second embodiment shown in FIG. 9 will be described as follows:

The upper cover part 300b includes the one oval-shaped upper central hole 310b (see FIG. 9(a)), the lower cover part 300a includes the one oval-shaped lower central hole 310a having the same size or a different size, and both the central holes are misaligned with each other (see FIG. 9(b)). When the lower and upper cover parts are coupled to each other, space "A1" of FIG. 9(c) is opened as the upper central hole 310b and the lower central hole 310a overlap each other. Meanwhile, when the upper cover part 300b is rotated clockwise, an open space may be partially increased, as in space "A2" of FIG. 9(d). Furthermore, when the upper cover part 300b is further rotated clockwise, an open space may be variable so that the open space is further increased as the two central holes 310a and 310b almost completely overlap each other, as in space "A3" of FIG. 9(e).

Figure 10A:
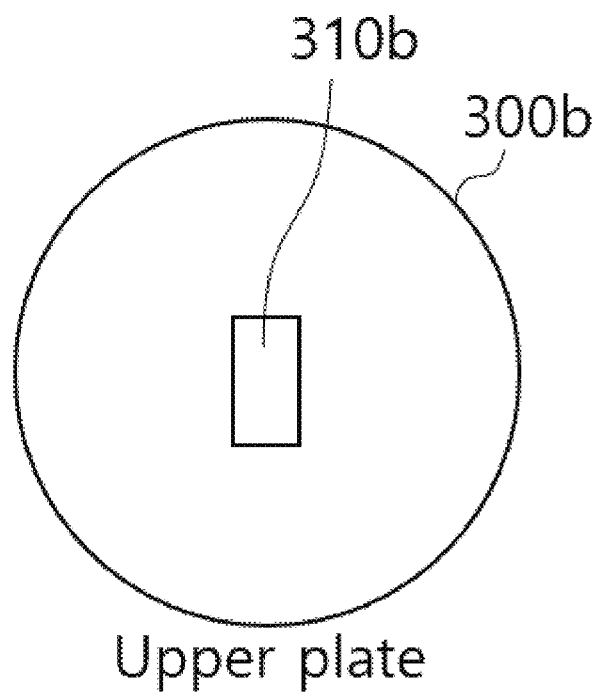
FIGS. 10(a), 10(b), 10(c), 10(d) and 10(e) show embodiments regarding the shape of central holes according to the present invention, in which the central holes have a rectangular shape.
Figure 10B:
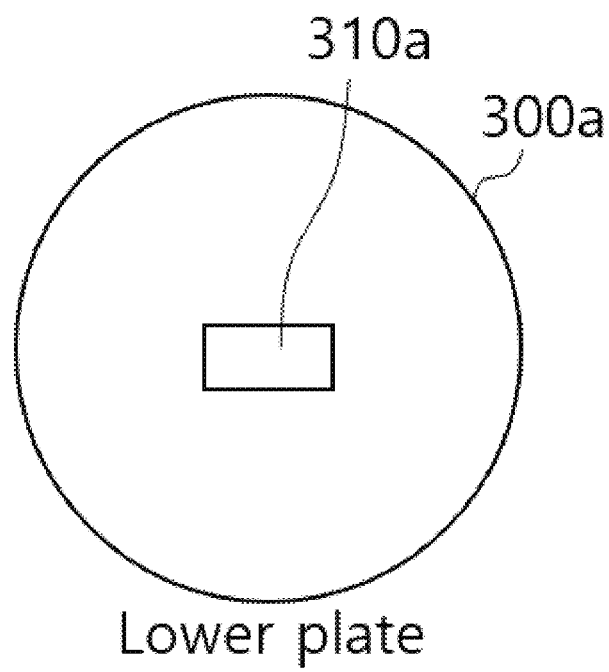
Figure 10C:
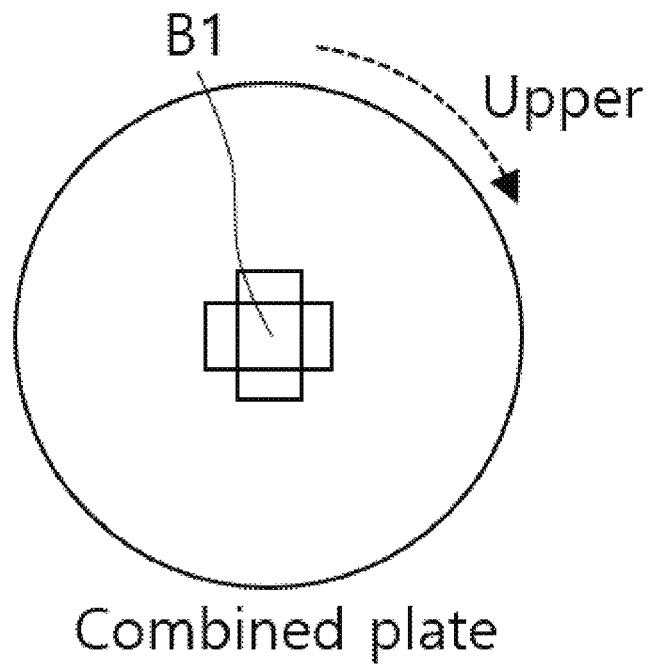
Figure 10D:
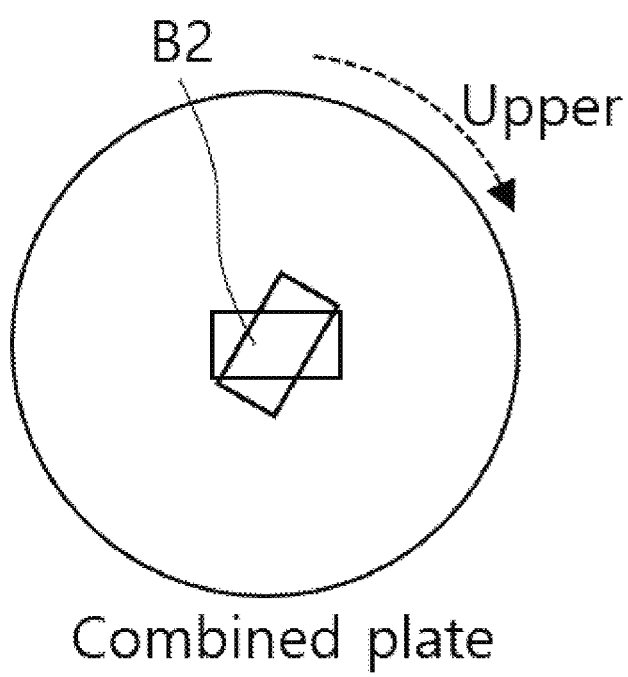
Figure 10E:
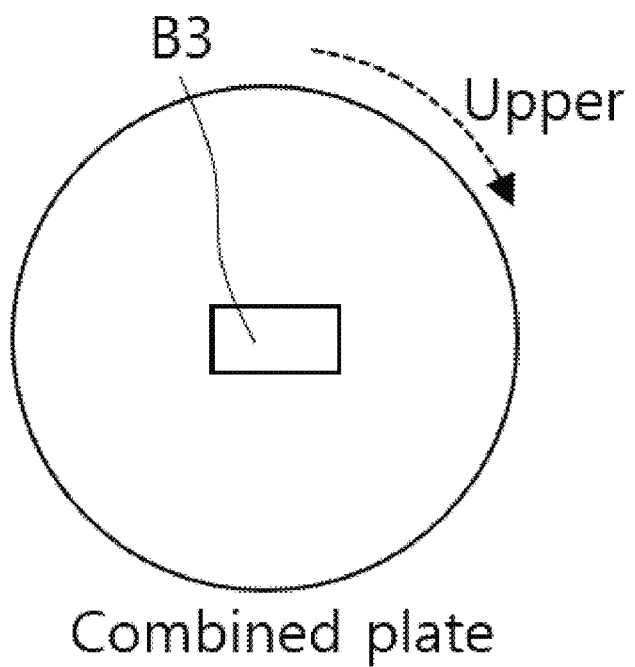

The operational structure of the second embodiment shown in FIG. 10 will be described as follows:

An upper cover part 300b includes one rectangular upper central hole 310b (see FIG. 10(a)), a lower cover part 300a includes one rectangular lower central hole 310a having the same size or a different size, and both the central holes are misaligned with each other (see FIG. 10(b)). When the lower and upper cover parts are coupled to each other, space "B1" of FIG. 10(c) is opened as the upper central hole 310b and the lower central hole 310a overlap each other. Meanwhile, when the upper cover part 300b is rotated clockwise, an open space may be partially increased, as in space "B2" of FIG. 10(d). Furthermore, when the upper cover part 300b is further rotated clockwise, the open space may be variable so that the open space is further increased as the two central holes 310a and 310b almost completely overlap each other, as in space "B3" of FIG. 10(e).

Various experimental examples using the energy concentrator according to the present invention will be described with reference to the drawings below.

Figure 11A:
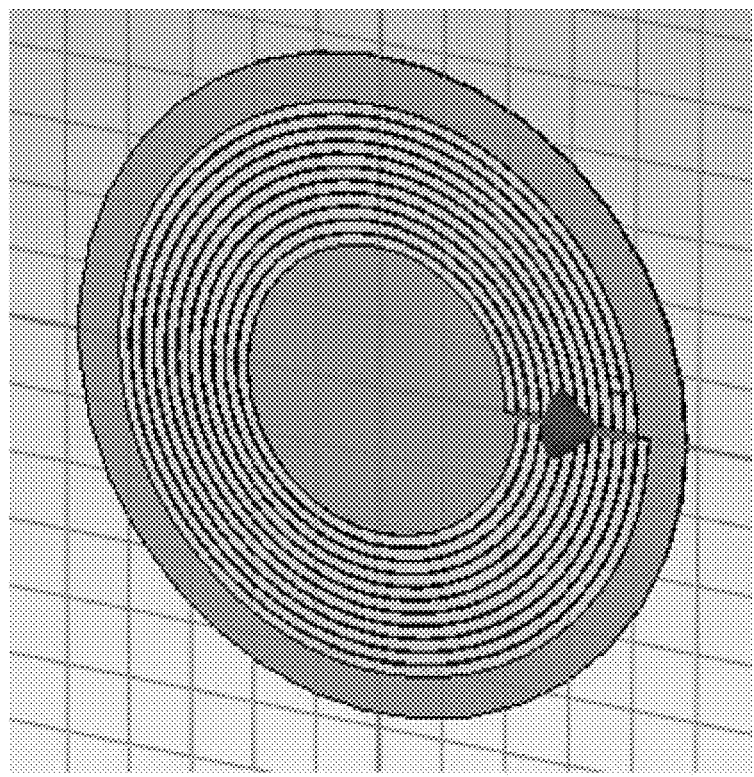
FIGS. 11(a) and 11(b) show shapes of a loop antenna coil configured to generate a magnetic field and the cross section of a generated magnetic field.

FIG. 11 shows the shape of a loop antenna coil configured to generate a magnetic field and the cross section of a generated magnetic field.

Figure 11B:
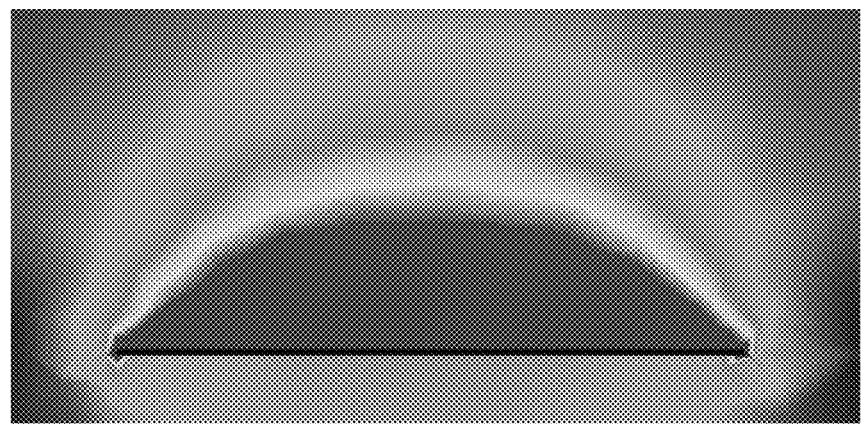

It can be seen that when an electrode is formed in the shape of a loop antenna coil as shown in FIG. 11, a magnetic field is formed. In this case, it is a common phenomenon that a maximum magnetic field appears at the center of the coil and a field distribution decreases toward both ends thereof, as shown in FIG. 11(b). In this field distribution, the reason why the magnetic field is not emitted not from the bottom surface but only from the top surface is that there is used a structure in which a magnetic material used to shield a magnetic field is disposed on the bottom surface when the coil electrode is formed.

Figure 12:
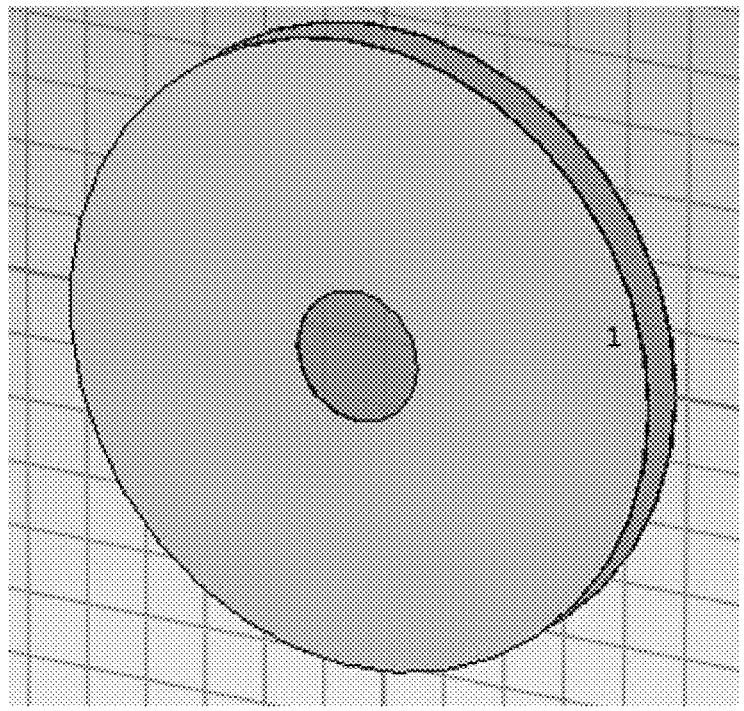
FIGS. 12(a) and 12(b) show structures in which a central hole is formed over an electrode in the form of a loop antenna coil by covering the electrode with a cover part having only the central hole and the cross section of a generated magnetic field.
Figure 12:
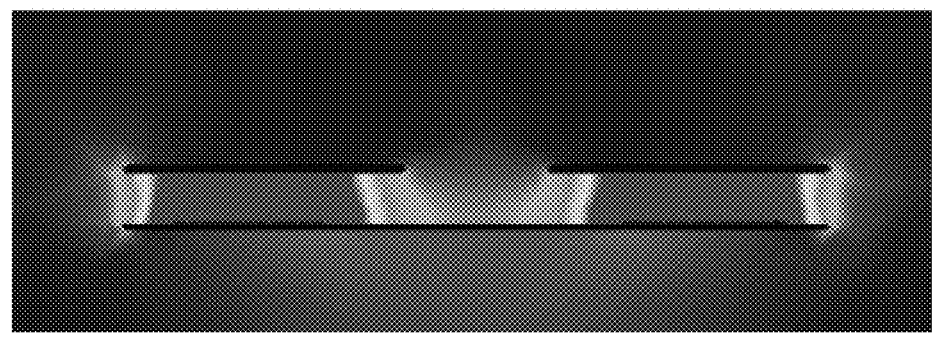

FIG. 12 shows a structure in which a central hole is formed over an electrode in the form of a loop antenna coil by covering the electrode with a cover part having only the central hole and the cross section of a generated magnetic field.

FIG. 12 shows the structure in which the central hole is formed over the electrode in the shape of a loop antenna coil by covering the electrode with the cover part made of an electrically conductive material such as a metal and having the central hole and the cross section of the magnetic field generated by this structure. The top of the coil is covered with the cover part made of an electrically conductive material such as metal in order to adjust the distribution of a magnetic field emitted through the coil electrode. In the case of a cover part made of an electrically conductive material and not having a central hole, the magnetic field may not pass through the cover part. Accordingly, the cover part made of an electrically conductive material and having a central hole is formed in order to pass a magnetic field through only a desired portion while basically blocking a magnetic field in a region covered with the cover part made of an electrically conductive material. However, it can be seen from the magnetic field distribution that the magnetic field does not pass through not only the region covered with the cover part made of an electrically conductive material but also the portion pierced by the central hole. Therefore, it can be seen that the magnetic field cannot be passed through a portion by simply forming the central hole in the cover part made of an electrically conductive material. The reason for this is that an electromotive force to hinder a change in magnetic flux on the surface of the electrically conductive conductor such as metal for the generated magnetic field is generated, which forms an inverse magnetic field by means of an eddy current in the form of a closed curve. As a result, even when the central hole is formed, the magnetic field cannot pass through the central hole.

Figure 13A:
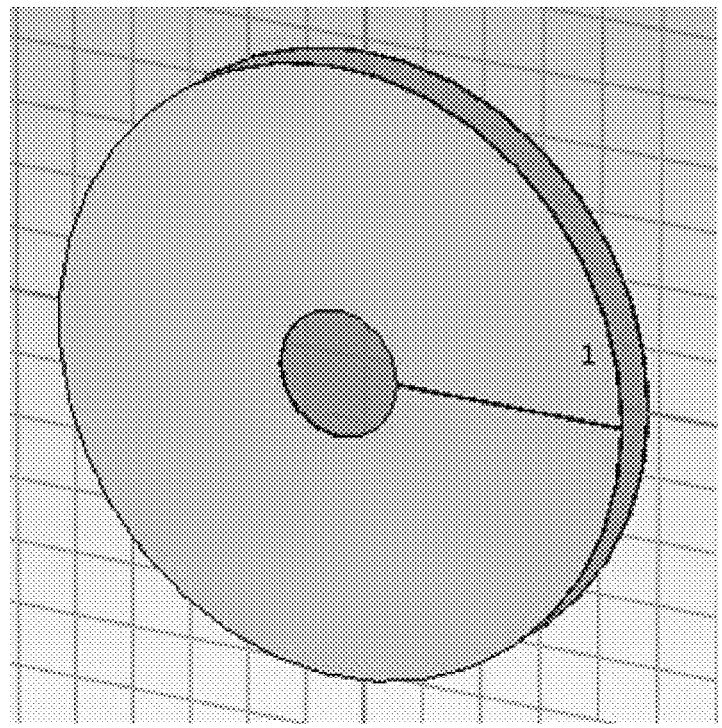
FIGS. 13(a) and 13(b) show structures in which a micro-slit is formed over an electrode in the form of a loop antenna coil by covering the electrode with a cover part having a central hole and the micro-slit and the cross section of a generated magnetic field.
Figure 13B:
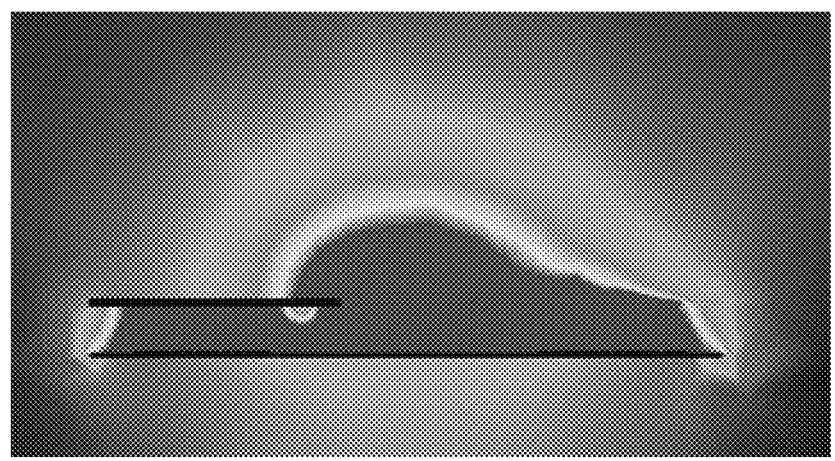

FIG. 13 shows a structure in which a micro-slit is formed over an electrode in the form of a loop antenna coil by covering the electrode with a cover part having a central hole and the micro-slit and the cross section of a generated magnetic field.

FIG. 13 shows the structure in which the micro-slit is formed over the electrode in the shape of a loop antenna coil by covering the electrode with the cover part made of an electrically conductive material and having the central hole and the micro-slit and the cross section of the magnetic field generated by this structure. Unlike in FIG. 12, the micro-slit is formed in the cover part made of an electrically conductive material. In this case, it can be seen that unlike in the magnetic field distribution shown in FIG. 12, a magnetic field passes through the portions in which the central hole and the micro-slit are formed and the passage of a magnetic field is suppressed in a region without a micro-slit. Therefore, unlike in the general magnetic field distribution of the coil electrode shown in FIG. 11, magnetic field energy can be passed through only a portion, so that the magnetic field distribution may be adjusted. In addition, it can be seen that the magnitude of the magnetic field in the inner center is increased due to this concentration effect.

Figure 14A:
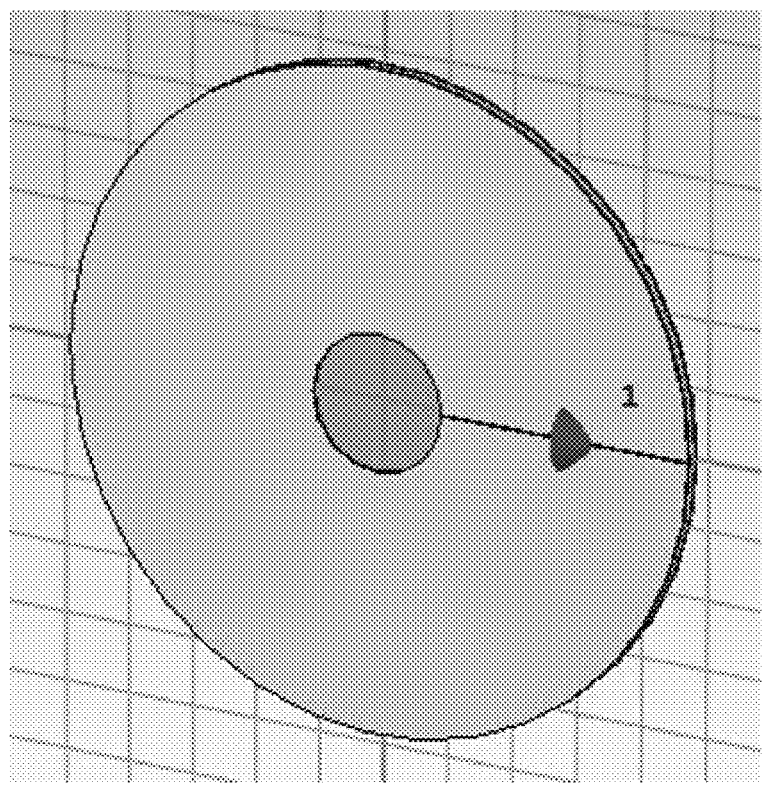
FIGS. 14(a) and 14(b) show structures in which the gap between a cover part and a coil electrode is 0.8 mm in a state in which the electrode in the shape of a loop antenna coil is covered with the cover part having a central hole and a micro-slit and the cross section of a generated magnetic field.
Figure 14B:
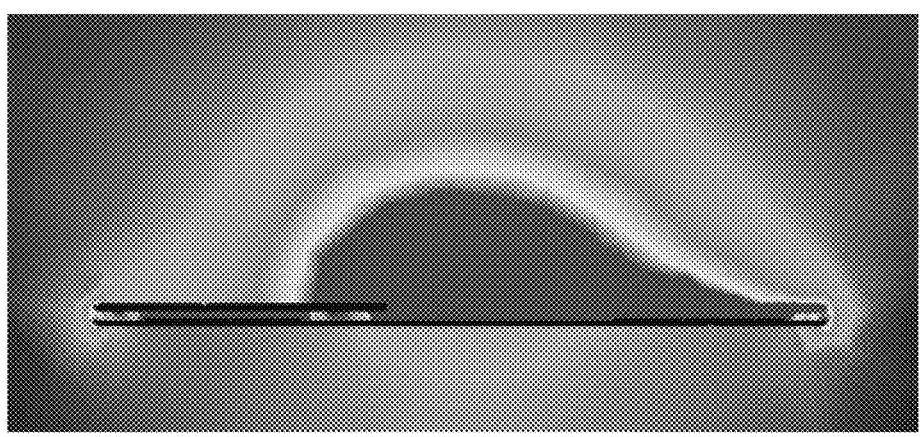

FIG. 14 shows a structure in which the gap between a cover part and a coil electrode is 0.8 mm in a state in which the electrode in the shape of a loop antenna coil is covered with the cover part having a central hole and a micro-slit and the cross section of a generated magnetic field.

FIG. 14 shows the structure in which the gap between the cover part made of an electrically conductive material and the coil electrode is 0.8 mm in a state in which the electrode in the shape of a loop antenna coil is covered with the cover part made of an electrically conductive material and having the central hole and the micro-slit and the cross section of the generated magnetic field. In FIG. 13, the gap between the cover part made of an electrically conductive material and the coil electrode is 3.8 mm. Accordingly, the case of FIG. 14 corresponds to a structure in which the gap between the coil electrode and the cover part made of an electrically conductive material is narrower than the gap in the case of FIG. 13. In this case, it can be seen that the magnetic field distribution is similar, but the magnitude of the magnetic field is higher in the center portion thereof.

Figure 15:
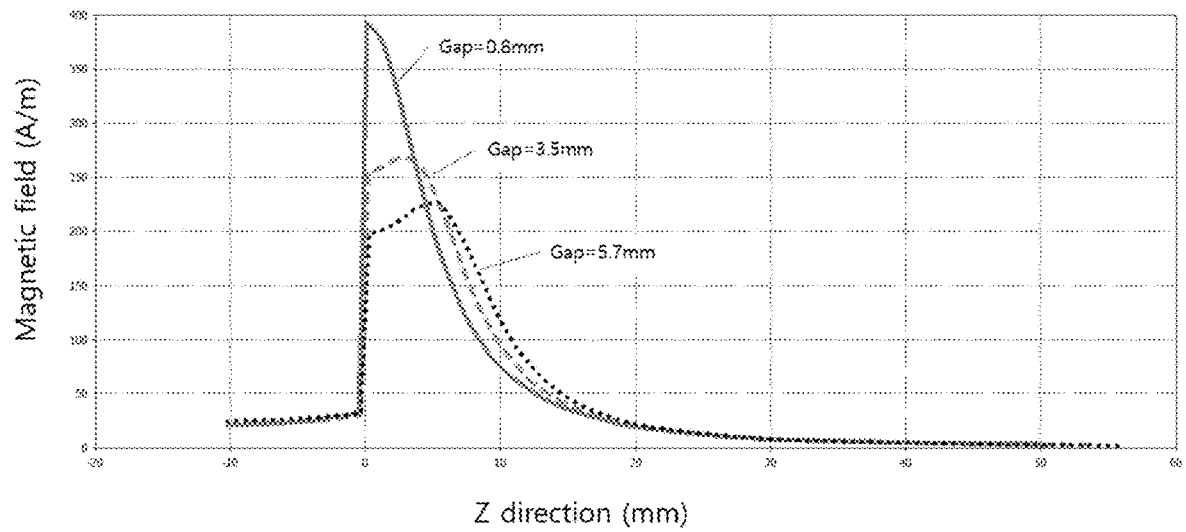
FIG. 15 is a graph showing comparisons between the magnitudes of electric field energy according to the gap between a cover part and a coil electrode in a state in which the coil electrode is covered with the cover part having a central hole and a micro-slit.

FIG. 15 is a graph showing comparisons between the magnitudes of electric field energy according to the gap between a cover part and a coil electrode in a state in which the coil electrode is covered with the cover part having a central hole and a micro-slit.

FIG. 15 shows the graph showing the comparisons between the magnitudes of electric field energy according to the gap between the cover part made of an electrically conductive material and the coil electrode in a state in which the coil electrode is covered with the cover part made of an electrically conductive material and having the central hole and the micro-slit. It can be seen that as the gap between the cover part made of an electrically conductive material and the coil electrode is decreased, magnetic field energy is concentrated, and thus the magnitude of a magnetic field increases. Therefore, it can be seen that the magnitude of concentrated magnetic field energy may be adjusted by adjusting the gap between the cover part made of an electrically conductive material and having a micro-slit and the coil electrode.

Figure 16A:
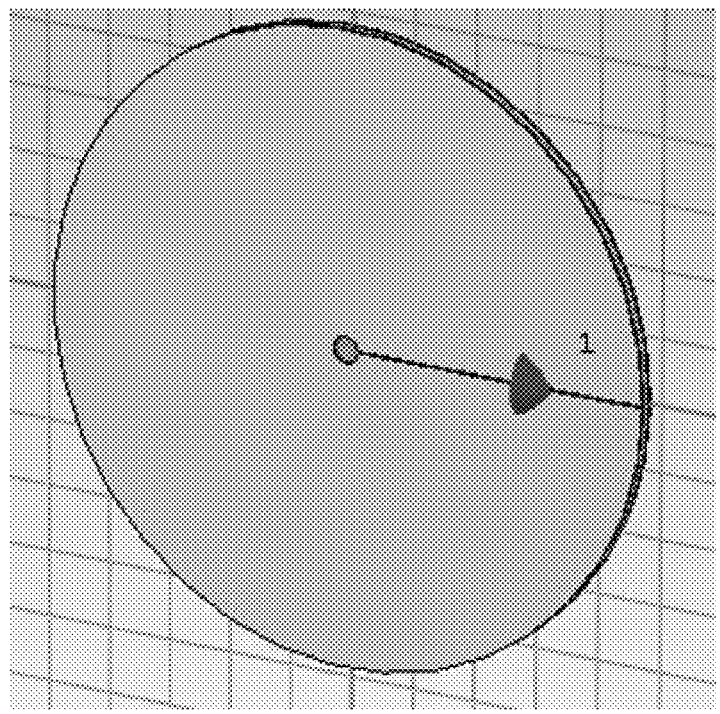
FIGS. 16(a) and 16(b) show structures in which a central hole has a radius of 1 mm in a state in which an electrode in the shape of a loop antenna coil is covered with a cover part having the central hole and a micro-slit and the cross section of a generated magnetic field.
Figure 16B:
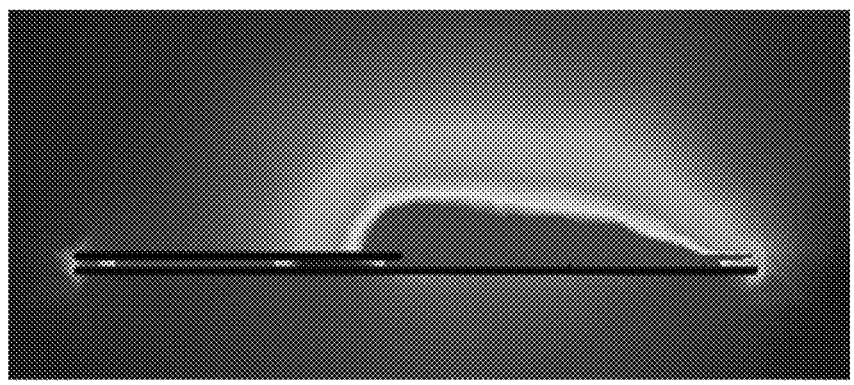

FIG. 16 shows a structure in which a central hole has a radius of 1 mm in a state in which an electrode in the shape of a loop antenna coil is covered with a cover part having the central hole and a micro-slit and the cross section of a generated magnetic field.

FIG. 16 shows the structure in which the central hole has a radius of 1 mm in a state in which the electrode in the shape of a loop antenna coil is covered with the cover part having the central hole and the micro-slit and the cross section of the generated magnetic field.

Figure 17:
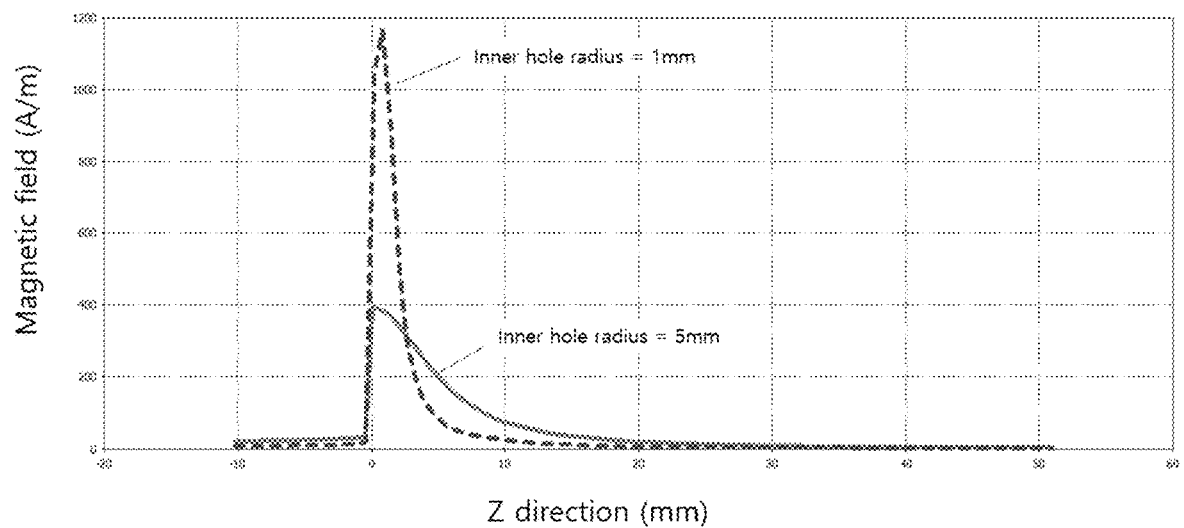
FIG. 17 shows a graph showing comparisons between the magnitudes of electric field energy according to the size of a central hole in a state in which a coil electrode is covered with a cover part having the central hole and a micro-slit.

FIG. 17 shows a graph showing comparisons between the magnitudes of electric field energy according to the size of a central hole in a state in which a coil electrode is covered with a cover part having the central hole and a micro-slit.

FIG. 17 shows the graph showing the comparisons according to the size of the central hole. In FIG. 14, the central hole has a radius of 5 mm. The case of FIG. 16 corresponds to a structure in which the size of the central hole is smaller. It can be seen that as the size of the central hole is decreased, magnetic field energy is concentrated, and thus the magnitude of a magnetic field is increased. Accordingly, it can be seen that the magnitude and area of concentrated magnetic field energy may be adjusted by adjusting the size of the central hole of the cover part made of an electrically conductive material and having a micro-slit.

Figure 18A:
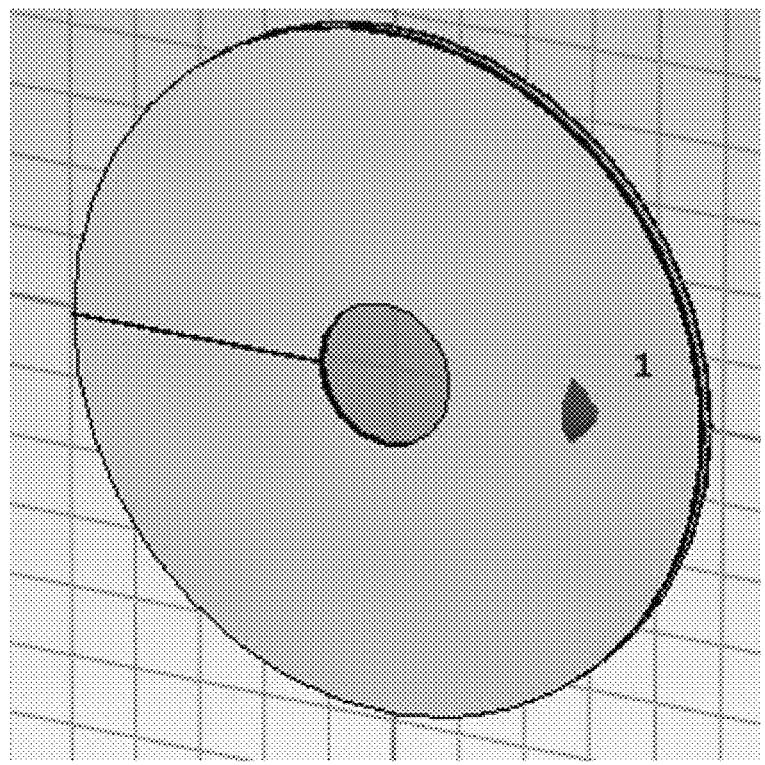
FIGS. 18(a) and 18(b) show shapes of a loop antenna coil in a state in which two cover parts each having a central hole and a micro-slit overlap each other in different micro-slit directions over an electrode in the form of a loop antenna coil and the cross section of a generated magnetic field.
Figure 18B:
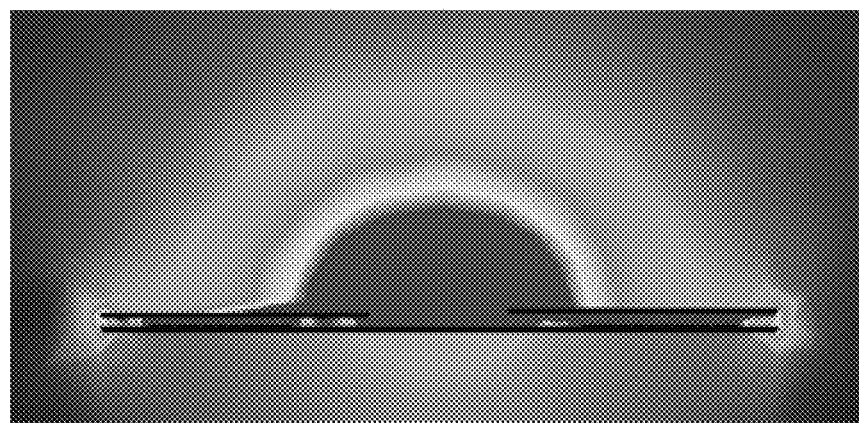

FIG. 18 shows the shape of a loop antenna coil in a state in which two cover parts each having a central hole and a micro-slit overlap each other in different micro-slit directions over an electrode in the form of a loop antenna coil and the cross section of a generated magnetic field.

FIG. 18 shows the shape of the loop antenna coil in a state in which the two cover parts made of an electrically conductive material and each having a central hole and a micro-slit overlap each other in the different micro-slit directions over the electrode in the form of a loop antenna coil and the cross section of the generated magnetic field. It can be seen from the magnetic field distribution that a magnetic field appears high in the region of the central hole and the magnetic field passes through the region of the micro-slit. As a method of allowing the magnetic field to pass through the region of the central hole and suppressing the passage of the magnetic field in the region of the micro-slit, the two cover parts made of an electrically conductive material are provided to overlap each other, but the directions in which micro-slits are formed are different. It can be seen from the magnetic field results that the magnetic field passes through only the region of the central hole and the magnetic field does not pass through the other parts. Therefore, by using this method, energy may be concentrated by passing the magnetic field through only a desired region, and the area onto which magnetic field energy is radiated may be accurately adjusted.

Figure 19A:
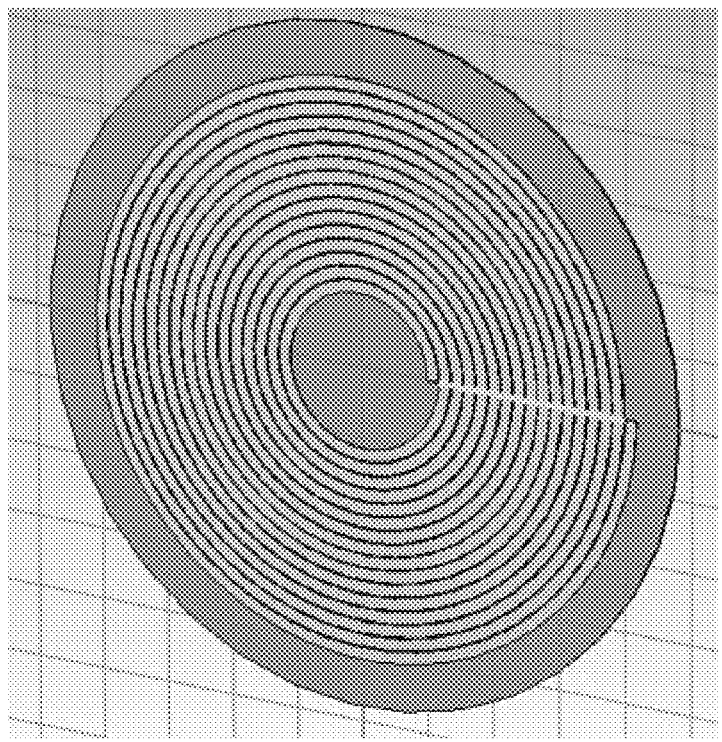
FIGS. 19(a), 19(b) and 19(c) show structures in which the number of turns of a coil in the shape of a loop antenna coil electrode is increased to 35 in a state in which the coil electrode is covered with a cover part having a central hole and a micro-slit and the cross section of a magnetic field generated by this structure.
Figure 19B:
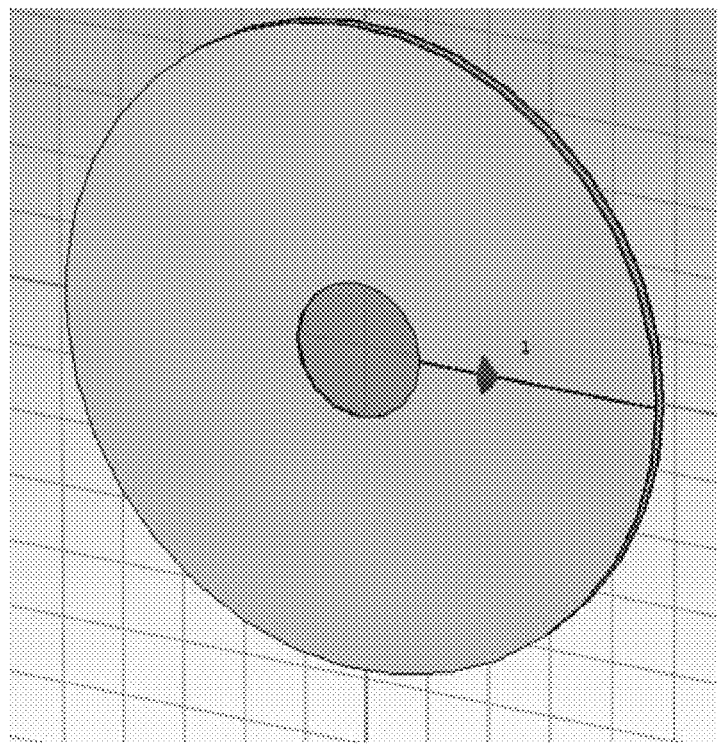
Figure 19C:
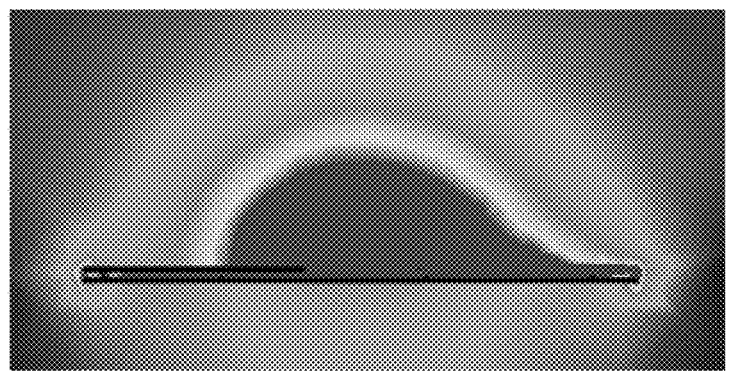

FIG. 19 shows a structure in which the number of turns of a coil in the shape of a loop antenna coil electrode is increased to 35 in a state in which the coil electrode is covered with a cover part having a central hole and a micro-slit and the cross section of a magnetic field generated by this structure.

Figure 20:
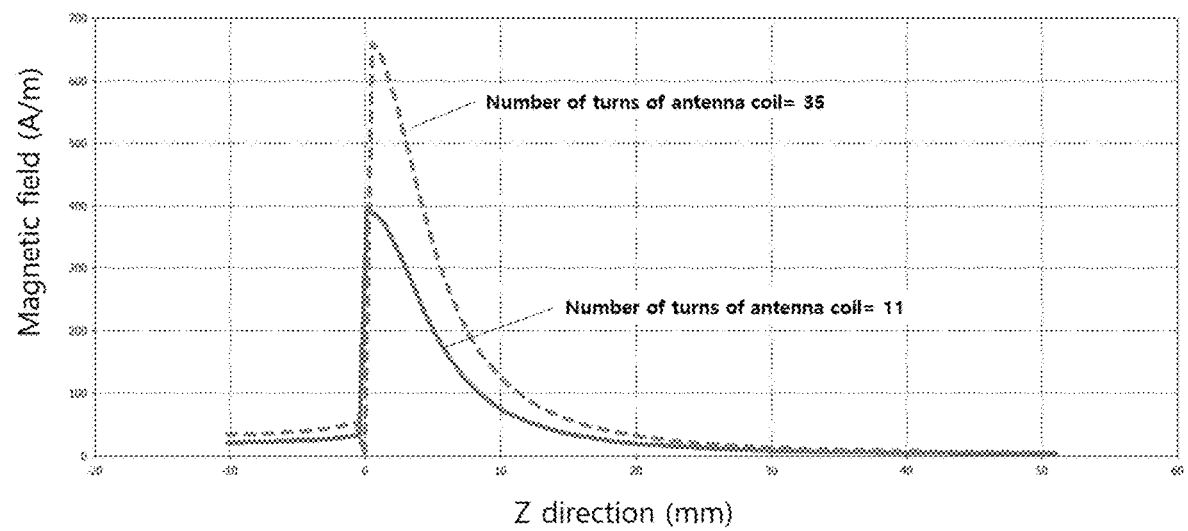
FIG. 20 shows a graph showing comparisons between the magnitudes of electric field energy according to the number of turns of an antenna coil electrode in a state in which the coil electrode is covered with a cover part having a central hole and a micro-slit.

FIG. 20 shows a graph showing comparisons between the magnitudes of electric field energy according to the number of turns of an antenna coil electrode in a state in which the coil electrode is covered with a cover part having a central hole and a micro-slit.

FIG. 20 shows the graph showing the comparisons according to the number of turns of the coil. In FIG. 14, the number of turns of the coil is 11. The case of FIG. 19 corresponds a structure in which the number of turns of the coil electrode is larger. It can be seen from the results that as the number of turns of the coil electrode is increased, magnetic field energy is concentrated, and thus the magnitude of the magnetic field increases. Therefore, it can be seen that the magnitude and region of concentrated magnetic field energy may be adjusted by adjusting the number of turns of the coil electrode.

The energy concentration apparatus having a central hole and a micro-slit according to the present invention have the following advantages:

A first advantage of the present invention is to obtain high energy by concentrating the energy formed on an electrode.

A second advantage of the present invention is to adjust the area to which energy is applied as desired by allowing energy to be radiated only onto a specific area of interest.

A third advantage of the present invention is to adjust the magnitude and region of concentrated energy by additionally forming a micro-slit structure over an electrode.

A fourth advantage of the present invention is to variably adjust the space to which energy is applied by using the micro-slits in a dual structure.

A fifth advantage of the present invention is to concentrate energy only by using a simple method of forming the micro-slit structure over the electrode without the construction of a complicated system in which a plurality of array electrodes is formed to concentrate energy.

A sixth advantage of the present invention is to adjust the amount and area of energy by adjusting a factor such as the shapes and positions of the micro-slits, the number of micro-slits, the diameter of the central holes, and/or the number of turns of the coil.

The advantages of the present invention are not limited to those mentioned above, and other advantages that are not mentioned will be clearly understood by those skilled in the art from the foregoing description.

The embodiments described in the present specification and the accompanying drawings are merely illustrative of some of the technical spirits included in the present invention. Therefore, it is obvious that the embodiments disclosed in the present specification are not intended to limit the technical spirit of the present invention, but are intended to illustrate the technical spirit, so that the scope of the technical spirit of the present invention is not limited to these embodiments. Modifications and specific embodiments that can be easily derived by those skilled in the art within the scope of the technical spirits included in the present specification and drawings of the present application should be interpreted as being included in the scope of the present invention.

What is claimed is:
1. An energy concentration apparatus comprising:
a body part;
a loop antenna coil part disposed on the body part; and
a cover part coupled to the body part in order to cover the loop antenna coil part;

wherein the cover part comprises a lower cover part and an upper cover part, the lower cover part is coupled to the body part in order to cover the loop antenna coil part;

the upper cover part is coupled to a top surface of the lower cover part, the lower cover part includes a lower central hole and at least one lower micro-slit, the upper cover part includes an upper central hole and at least one upper micro-slit; and at least one of the lower cover part and the upper cover part is rotatably provided, and an exposed space is variable as the central holes and the micro-slits overlap each other through rotation.

2. The energy concentration apparatus of claim 1, wherein:

the lower cover part and the upper cover parts are made of an electrically conductive material; and a bottom surface of the body part is provided with a magnetic material.

3. The energy concentration apparatus of claim 1, wherein the micro-slit of each cover part is formed to continuously connect the central hole of the cover part and an outer circumference of the cover part.

4. The energy concentration apparatus of claim 3, wherein each micro-slit is formed such that a width of an outer end thereof in contact with the outer circumference is wider than a width of an inner end thereof in contact with the central hole.

5. The energy concentration apparatus of claim 3, wherein each micro-slit is formed such that a width of an outer end thereof in contact with the outer circumference is narrower than a width of an inner end thereof in contact with the central hole.

6. The energy concentration apparatus of claim 3, wherein each micro-slit is formed such that a width of a central portion thereof is wider than a width of inner and outer ends thereof.

7. The energy concentration apparatus of claim 3, wherein each micro-slit is formed such that a width of a central portion thereof is narrower than a width of inner and outer ends thereof.

8. An energy concentration apparatus comprising:
a body part;
a loop antenna coil part disposed on the body part;
a lower cover part coupled to the body part in order to cover the loop antenna coil part;
an upper cover part coupled to a top surface of the lower cover part in a corresponding shape;
a drive unit configured to drive the upper cover part; and
a control unit configured to control the drive unit;
wherein the lower cover part includes a lower central hole and at least one lower micro-slit, and the upper cover part includes an upper central hole and at least one upper micro-slit; and
wherein at least one of the lower cover part and the upper cover part is rotatably provided, and an exposed space is variable as the central holes and the micro-slits overlap each other through rotation.

9. The energy concentration apparatus of claim 8, wherein:

the cover part or lower and upper cover parts are made of an electrically conductive material; and a bottom surface of the body part is provided with a magnetic material.

10. The energy concentration apparatus of claim 8, wherein the micro-slit of each cover part is formed to continuously connect the central hole of the cover part and an outer circumference of the cover part.

11. The energy concentration apparatus of claim 10, wherein each micro-slit is formed such that a width of an outer end thereof in contact with the outer circumference is wider than a width of an inner end thereof in contact with the central hole.

12. The energy concentration apparatus of claim 10, wherein each micro-slit is formed such that a width of an outer end thereof in contact with the outer circumference is narrower than a width of an inner end thereof in contact with the central hole.

13. The energy concentration apparatus of claim 10, wherein each micro-slit is formed such that a width of a central portion thereof is wider than a width of inner and outer ends thereof.

14. The energy concentration apparatus of claim 10, wherein each micro-slit is formed such that a width of a central portion thereof is narrower than a width of inner and outer ends thereof.

15. The energy concentration apparatus of claim 8, wherein energy is selectively concentrated by adjusting a diameter of each central hole, a width of each micro-slit, and/or a number of turns of a coil wound in the loop antenna coil part.

16. The energy concentration apparatus of claim 8, wherein the upper micro-slit has a width that is equal to or narrower than a width of the lower micro-slit.

17. The energy concentration apparatus of claim 8, wherein:

the lower cover part includes one lower micro-slit;
the upper cover part includes a plurality of upper micro-slits having different widths; and
the widths of the upper micro-slits are equal to or narrower than a width of the lower micro-slit.

18. The energy concentration apparatus of claim 8, wherein when at least one of the lower and upper cover parts is rotated, the upper micro-slit overlaps the lower micro-slit.

19. The energy concentration apparatus of claim 8, wherein:

each of the central holes has an oval shape or eccentric circle shape; and
when at least one of the lower and upper cover parts is rotated, an exposed space of the central holes is variable as the central holes partially overlap each other.

20. The energy concentration apparatus of claim 8, wherein:

each of the central holes has an elongated polygonal shape; and
when at least one of the lower and upper cover parts is rotated, an exposed space of the central holes is variable as the central holes partially overlap each other.

* * * * *